US006277865B1

(12) United States Patent
Klein et al.

(10) Patent No.: US 6,277,865 B1
(45) Date of Patent: *Aug. 21, 2001

(54) PIPERIDIDINYL AND N-AMIDINOPIPERIDINYL DERIVATIVES

(75) Inventors: Scott I. Klein, Norristown, PA (US); Kevin R. Guertin, Verona, NJ (US)

(73) Assignee: Aventis Pharmaceuticals Products Inc., Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/273,618

(22) Filed: Mar. 22, 1999

Related U.S. Application Data

(63) Continuation-in-part of application No. 08/884,405, filed on Jun. 27, 1997, now Pat. No. 6,080,767.
(60) Provisional application No. 60/079,002, filed on Mar. 23, 1998.

(51) Int. Cl.[7] ...................... A61K 31/445; C07D 401/10; C07D 401/12
(52) U.S. Cl. .......................... 514/318; 514/314; 514/326; 514/331; 514/357; 546/193; 546/210; 546/223; 546/265; 546/272.7
(58) Field of Search ...................................... 546/193, 201, 546/272.7, 223, 265; 514/314, 318, 326, 331, 357

(56) References Cited

U.S. PATENT DOCUMENTS

| 4,916,145 | * | 4/1990 | Tilley et al. ........................ 514/357 |
| 5,648,368 | * | 7/1997 | Egbertson et al. .................. 514/331 |
| 5,741,799 | * | 4/1998 | Kimball et al. ..................... 514/316 |
| 5,744,486 |   | 4/1998 | Sanderson et al. . |
| 5,852,045 |   | 12/1998 | Askew et al. . |

FOREIGN PATENT DOCUMENTS

97/24118 * 7/1997 (WO) .

OTHER PUBLICATIONS

Zablocki et al. "Potent in vitro and invivo inhibitor os platelet aggregation . . . " J. Med. Chem. v.36, p. 1811–1819, 1993.*

* cited by examiner

Primary Examiner—Ceila Chang
(74) Attorney, Agent, or Firm—Raymond S. Parker, III; Irving Newman; Peter J. Butch, III

(57) ABSTRACT

This invention is directed to a compound of formula I which is useful for inhibiting the activity of Factor Xa, by combining said compound with a composition containing Factor Xa. The present invention is also directed to compositions containing compounds of the formula I, methods for their preparation, their use, such as in inhibiting the formation of thrombin or for treating a patient suffering from, or subject to, a disease state associated with a physiologically detrimental excess amount of thrombin.

39 Claims, No Drawings

PIPERIDIDINYL AND N-AMIDINOPIPERIDINYL DERIVATIVES

This application is a continuation-in-part application of U.S. patent application Ser. No. 08/884,405 filed Jun. 27, 1997, now U.S. Pat. No. 6,080,767. This application also claims priority benefit under 35 U.S.C. §119(e) of U.S. provisional application Serial No. 60/079,002, filed Mar. 23, 1998.

FIELD OF THE INVENTION

The compounds of formula I are useful for inhibiting the activity of Factor Xa, and also, exhibit useful pharmacological activity. Accordingly the compounds are incorporated into pharmaceutical compositions and used in the treatment of patients suffering from certain medical disorders. More especially, they are Factor Xa inhibitors. The present invention is directed to compounds of formula I, intermediates thereof, compositions containing compounds of formula I, and their use, inclusive of inhibiting Factor Xa and treating a patient suffering from, or subject to, physiological conditions amelioratable by administering to said patient a pharmaceutically acceptable amount of said inhibitor of Factor Xa.

Factor Xa is the penultimate enzyme in the coagulation cascade. Both free Factor Xa and Factor Xa assembled in the prothrombinase complex (Factor Xa, Factor Va, calcium and phospholipid) are inhibited by compounds of formula I. Factor Xa inhibition is obtained by direct complex formation between the inhibitor and the enzyme and is therefore independent of the plasma cofactor antithrombin III. Effective Factor Xa inhibition is achieved by administering the compounds either by oral administration, continuous intravenous infusion, bolus intravenous administration or any other parenteral route such that it achieves the desired effect of preventing the Factor Xa induced formation of thrombin from prothrombin.

Anticoagulant therapy is indicated for the treatment and prophylaxis of a variety of thrombotic conditions of both the venous and arterial vasculature. In the arterial system, abnormal thrombus formation is primarily associated with arteries of the coronary, cerebral and peripheral vasculature. The diseases associated with thrombotic occlusion of these vessels principally include acute myocardial infarction (AMI), unstable angina, thromboembolism, acute vessel closure associated with thrombolytic therapy and percutaneous transluminal coronary angioplasty (PTCA), transient ischemic attacks, stroke, intermittent claudication and bypass grafting of the coronary (CABG) or peripheral arteries. Chronic anticoagulant therapy may also be beneficial in preventing the vessel luminal narrowing (restenosis) that often occurs following PTCA and CABG, and in the maintenance of vascular access patency in long-term hemodialysis patients. With respect to the venous vasculature, pathologic thrombus formation frequently occurs in the veins of the lower extremities following abdominal, knee and hip surgery (deep vein thrombosis, DVT). DVT further predisposes the patient to a higher risk of pulmonary thromboembolism. A systemic, disseminated intravascular coagulopatby (DIC) commonly occurs in both vascular systems during septic shock, certain viral infections and cancer. This condition is characterized by a rapid consumption of coagulation factors and their plasma inhibitors resulting in the formation of life-threatening clots throughout the microvasculature of several organ systems. The indications discussed above include some, but not all, of the possible clinical situations where anticoagulant therapy is warranted. Those experienced in this field are well aware of the circumstances requiring either acute or chronic prophylactic anticoagulant therapy.

SUMMARY OF THE INVENTION

This invention is directed to a compound of formula I which is useful for inhibiting the activity of Factor Xa, by combining said compound with a composition containing Factor Xa, where said compound is as follows:

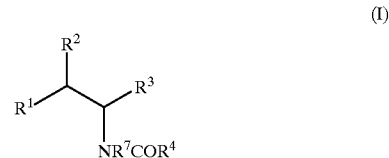

wherein $R^1$ is a group of formula

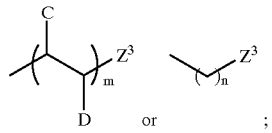

$R^2$ is hydrogen, $-CO_2R^5$, $-C(O)R^5$, $-CONR^5R^5$, $-CH_2OR^6$ or $-CH_2SR^6$;

$R^3$ is hydrogen, optionally substituted alkyl, $Z^1$-alkyl, or a group of formula

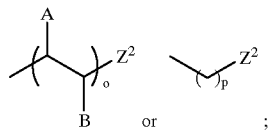

$R^4$ is alkyl, alkenyl, alkynyl, optionally substituted cycloalkyl, optionally substituted cycloalkenyl, optionally substituted heterocyclyl, optionally substituted heterocyclenyl, optionally substituted aryl, optionally substituted heteroaryl, optionally substituted aralkyl, optionally substituted heteroaralkyl, optionally substituted aralkenyl, optionally substituted beteroaralkenyl, optionally substituted aralkynyl, or optionally substituted heteroaralkynyl;

$R^5$ is hydrogen or lower alkyl;

$R^6$ is hydrogen, lower alkyl, $Z^2$-(lower alkyl), lower acyl, aroyl or heteroaroyl;

$R^7$ is hydrogen or lower alkyl;

A and B are hydrogen or taken together are a bond;

C and D are hydrogen or taken together are a bond;

$Z^1$ is $R^6-$ or $R^6S-$ or $Y^1Y^2N-$;

$Z^2$ is optionally substituted aryl, optionally substituted heteroaryl, optionally substituted cycloalkyl, optionally substituted cycloalkenyl, optionally substituted heterocyclyl, and optionally substituted heterocyclenyl;

$Z^3$ is substituted aryl, substituted cycloalkyl, substituted cycloalkenyl, optionally substituted heteroaryl, optionally substituted heterocyclyl, optionally substituted heterocyclenyl, substituted fused arylcycloalkyl, substituted fused arylcycloalkenyl, optionally substituted fused heteroarylcycloalkyl, optionally substituted fused heteroarylcycloalkenyl, optionally substituted fused heteroarylheterocyclyl, optionally substituted fused heteroarylheterocyclenyl, wherein at least one of the ring system substituents contains at least one basic nitrogen atom, or at least one nitrogen atom is incorporated in the ring system of the heteroaryl, heterocyclyl or heterocyclenyl moiety;

$Y^1$ and $Y^2$ are independently hydrogen, alkyl, aryl, aralkyl, acyl or aroyl; and m and o are independently 1 or 2;

n and p are independently 0, 1 or 3; or a pharmaceutically acceptable salt thereof, an N-oxide thereof, a solvate thereof, an acid bioisostere thereof, or prodrug thereof, provided that $Z^3$ is other than phenyl when substituted by a moiety of the formula

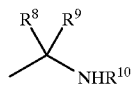

wherein $R^8$ and $R^9$ are hydrogen or together are $=NR^{11}$, wherein $R^{10}$ and $R^{11}$ are hydrogen.

The present invention is also directed to compositions containing compounds of the formula I, methods for their preparation, their use, such as in inhibiting the formation of thrombin or for treating a patient suffering from, or subject to, a disease state associated with a physiologically detrimental excess amount of thrombin.

DETAILED DESCRIPTION OF THE INVENTION

As used above, and throughout the description of the invention, the following terms, unless otherwise indicated, shall be understood to have the following meanings:

Definitions

"Acid bioisostere" means a group which has chemical and physical similarities producing broadly similar biological properties to a carboxy group (see Lipinski, Annual Reports in Medicinal Chemistry, 1986, 21, p.283 "Bioisosterism In Drug Design"; Yun, Hwahak Sekye, 1993, 33, p.576–579 "Application Of Bioisosterism To New Drug Design"; Zhao, Huaxue Tongbao, 1995, p.34–38 "Bioisosteric Replacement And Development Of Lead Compounds In Drug Design"; Grahain, Theochem, 1995, 343, p. 105–109 "Theoretical Studies Applied To Drug Design:ab initio Electronic Distributions In Bioisosteres"). Examples of suitable acid bioisosteres include: —C(=O)—NHOH, —C(=O)—CH$_2$OH, —C(=O)—CH$_2$SH, —C(=O)—NH—CN, sulpho, phosphono, alkylsulphonylcarbamoyl, tetrazolyl, arylsulphonylcarbamoyl, heteroarylsulphonylcarbamoyl, N-methoxycarbamoyl, 3-hydroxy-3-cyclobutene-1,2-dione, 3,5-dioxo-1,2,4-oxadiazolidinyl or heterocyclic phenols such as 3-hydroxyisoxazolyl and 3-hydoxy-1-methylpyrazolyl.

"Acylamino" is an acyl-NH— group wherein acyl is as defined herein.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably about 2 to about 4 carbon atoms in the chain. Branched means that one or more lower alkyl groups such as methyl, ethyl or propyl are attached to a linear alkenyl chain. "Lower alkenyl" means about 2 to about 4 carbon atoms in the chain which may be straight or branched. The alkenyl group may be substituted by one or more halo or cycloalkyl group. Exemplary alkenyl groups include ethenyl, propenyl, n-butenyl, i-butenyl, 3-methylbut-2-enyl, n-pentenyl, heptenyl, octenyl, cyclohexylbutenyl and decenyl. "Alkenylene" means a

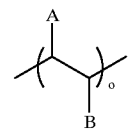

group wherein A and B form a direct bond and o is 1 or 2; or a

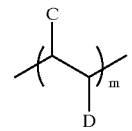

group, wherein C and D form a direct bond and m is 1 or 2.

"Alkoxy" means an alkyl-O— group wherein the alkyl group is as herein described. Exemplary alkoxy groups include methoxy, ethoxy, n-propoxy, i-propoxy, n-butoxy and heptoxy.

"Alkoxyalkyl" means an alkyl-O-alkyl- group wherein the alkyl groups are independent as herein described. Exemplary alkoxy groups include methoxyethyl, ethoxymethyl, n-butoxymethyl and cyclopentylmethyloxyethyl.

"Alkoxycarbonyl" means an alkyl-O—CO— group, wherein the alkyl group is as herein defined. Exemplary alkoxycarbonyl groups include methoxycarbonyl, ethoxycarbonyl, or t-butyloxycarbonyl.

"Alkyl" means an aliphatic hydrocarbon group which may be straight or branched having about 1 to about 20 carbon atoms in the chain. Preferred alkyl groups have 1 to about 12 carbon atoms in the chain. Branched means that one or more lower alkyl groups such as methyl, ethyl or propyl are attached to a linear alkyl chain. "Lower alkyl" means about 1 to about 4 carbon atoms in the chain which may be straight or branched. The alkyl may be substituted with one or more "alkyl group substituents" which may be the same or different, and include halo, cycloalkyl, carboxy, alkoxycarbonyl, aralkyloxycarbonyl, heteroaralkyloxycarbonyl or $Y^1Y^2NCO$—, wherein $Y^1$ and $Y^2$ are independently hydrogen, optionally substituted alkyl, optionally substituted aryl, optionally substituted aralkyl or optionally substituted heteroaralkyl, or $Y^1$ and $Y^2$ taken together with the N through which $Y^1$ and $Y^2$ are linked form a 4 to 7 membered heterocyclyl. Exemplary alkyl groups include methyl, trifluoromethyl, cyclopropylmethyl, cyclopentylmethyl, ethyl, n-propyl, i-propyl, n-butyl, t-butyl, n-pentyl, 3-pentyl, carboxymethyl, methoxycarbonylethyl, benzyloxycarbonylmethyl, pyridylmethyloxycarbonylmethyl.

"Alkylsulfinyl" means an alkyl-SO— group wherein the alkyl group is as defined above. Preferred groups are those wherein the alkyl group is lower alkyl.

"Alkylsulfonyl" means an alkyl-SO$_2$— group wherein the alkyl group is as defined above. Preferred groups are those wherein the alkyl group is lower alkyl.

"Alkylthio" means an alkyl-S— group wherein the alkyl group is as herein described. Exemplary alkylthio groups include methylthio, ethylthio, i-propylthio and heptylthio.

"Alkynyl" means an aliphatic hydrocarbon group containing a carbon-carbon triple bond and which may be straight or branched having about 2 to about 15 carbon atoms in the chain. Preferred alkynyl groups have 2 to about 12 carbon atoms in the chain; and more preferably about 2 to about 4 carbon atoms in the chain. Branched means that one or more lower alkyl groups such as methyl, ethyl or propyl are attached to a linear alkynyl chain. "Lower alkynyl" means about 2 to about 4 carbon atoms in the chain which may be straight or branched. The alkynyl group may be substituted by one or more halo. Exemplary alkynyl groups include ethynyl, propynyl, n-butynyl, 2-butynyl, 3-methylbutynyl, n-pentynyl, heptynyl, octynyl and decynyl.

"Amidino" or "amidine" means a group of formula

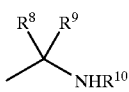

wherein $R^8$ and $R^9$ together are $=NR^{11}$ wherein $R^{11}$ is selected from hydrogen, $R^{12}O_2C-$, $R^{12}O-$, $HO-$, $R^{12}C(O)-$, $HCO-$, cyano, optionally substituted lower alkyl, nitro or $Y^{1a}Y^{2a}N-$; $R^{10}$ is selected from hydrogen, $HO-$, optionally substituted lower alkyl, optionally substituted aralkyl, optionally substituted heteroaralkyl, and $R^{12}O_2C-$; wherein $R^{12}$ is independently alkyl, optionally substituted aralkyl, or optionally substituted heteroaralkyl; and $Y^{1a}$ and $Y^{2a}$ are independently hydrogen or alkyl. Preferred amidino groups are those in which $R^8$ and $R^9$ are $=NR^{11}$, wherein $R^{11}$ is selected from hydrogen, $HO-$, $R^{12}O$, or optionally substituted lower alkyl and $R^{10}$ is as defined above. More preferred amidino groups are those in which $R^8$ and $R^9$ are $=NR^{11}$, and $R^{10}$ and $R^{11}$ are independently hydrogen, $HO-$, and $R^{12}O_2C-$.

"Amino acid" means an amino acid selected from the group consisting of natural and unnatural amino acids as defined herein. Preferred amino acids are those possessing an α-amino group. The amino a acids may be neutral, positive or negative depending on the substituents in the side chain. "Neutral amino acid" means an amino acid containing uncharged side chain substituents. Exemplary neutral amino acids include alanine, valine, leucine, isoleucine, proline, phenylalanine, tryptophan, methionine, glycine, serine, threonine and cysteine. "Positive amino acid" means an amino acid in which the side chain substituents are positively charged at physiological pH. Exemplary positive amino acids include lysine, arginine and histidine. "Negative amino acid" means an amino acid in which the side chain substituents bear a net negative charge at physiological pH. Exemplary negative amino acids include aspartic acid and glutamic acid. Preferred amino acids are α-amino acids. The more preferred amino acids are α-amino acids having L-stereochemistry at the α-carbon. Exemplary natural amino acids are isoleucine, proline, phenylalanine, tryptophan, methionine, glycine, serine, threonine, cysteine, tyrosine, asparagine, glutamine, lysine, arginine, histidine, aspartic acid and glutamic acid.

"Amine protecting group" means an easily removable group which is known in the art to protect an amino group against undesirable reaction during synthetic procedures and to be selectively removable. The use of amine protecting groups is well known in the art for protecting groups against undesirable reactions during a synthetic procedure and many such protecting groups are known, cf, for example, T. H. Greene and P. G. M. Wuts, Protective Groups in Organic Synthesis, 2nd edition, John Wiley & Sons, New York (1991), incorporated herein by reference. Preferred amine protecting groups are acyl, including formyl, acetyl, chloroacetyl, trichloroacetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl and the like, and acyloxy including methoxycarbonyl, 9-fluorenylmethoxycarbonyl, 2,2,2-trifluoroethoxycarbonyl, 2-trimethylsilylethxoycarbonyl, vinyloxycarbonyl, allyloxycarbonyl, 1-butyloxycarbonyl (BOC), 1,1 - dimethylpropynyloxycarbonyl, benzyloxycarbonyl (CBZ), p-nitrobenzyloxycarbony, 2,4-dichlorobenzyloxycarbonyl, and the like.

"Acid labile amine protecting group" means an amine protecting group as defined above which is readily removed by treatment with acid while remaining relatively stable to other reagents. A preferred acid labile amine protecting group is tert-butoxycarbonyl (BOC).

"Hydrogenation labile amine protecting group" means an amine protecting group as defined above which is readily removed by hydrogenation while remaining relatively stable to other reagents. A preferred hydrogenation labile amine protecting group is benzyloxycarbonyl (CBZ).

"Hydrogenation labile acid protecting group" means an acid protecting group as defined above which is readily removed by hydrogenation while remaining relatively stable to other reagents. A preferred hydrogenation labile acid protecting group is benzyl.

"Aralkoxycarbonyl" means an aralkyl-O—CO— group wherein the aralkyl groups is as herein described. An exemplary aralkoxycarbonyl group is benzyloxycarbonyl.

"Aralkyl" means an aryl-alkyl- group wherein the aryl and alkyl are as herein described. Preferred aralkyls contain a lower alkyl moiety. Exemplary aralkyl groups include benzyl, 2-phenethyl and naphthlenemethyl.

"Aralkylamino" means an aryl-alkyl-NH— group wherein aryl and alkyl are as defined herein.

"Aralkylthio" means an aralkyl-S— group wherein the aralkyl group is as herein described. An exemplary aralkylthio group is benzylthio.

"Aromatic" means aryl or heteroaryl as defined below. Preferred aromatic groups include phenyl, halo substituted phenyl and azaheteroaryl.

"Aroyl" means an aryl-CO— group wherein the aryl group is as herein described. Exemplary groups include benzoyl and 1- and 2-naphthoyl.

"Aroylamino" is an aroyl-NH— group wherein aroyl is as defined herein.

"Aryl" means an aromatic monocyclic or multicyclic ring system of about 6 to about 14 carbon atoms, preferably of about 6 to about 10 carbon atoms. The aryl is optionally substituted with one or more "ring system substituents" which may be the same or different, and are as defined herein. Representative aryl groups include phenyl or naphthyl, or phenyl substituted or naphthyl substituted.

"Aryldiazo" means an aryl-az- group wherein the aryl and azo groups are as defined herein.

"Fused arylcycloalkenyl" means a fused aryl and cycloalkenyl as defined herein. Preferred fused arylcycloalkenyl s are those wherein the aryl thereof is phenyl and the cycloalkenyl consists of about 5 to about 6 ring atoms. A fused arylcycloalkenyl as a variable may be bonded through any atom of the ring system there of capable of such. The fused arylcycloalkenyl may be optionally substituted by one or more ring system substituent, wherein the "ring system substituent" is as defined herein. Representative fused arylcycloalkenyl include 1,2-dihydronaphthylene, indene, and the like.

"Fused arylcycloalkyl" means a fused aryl and cycloalkyl as defined herein. Preferred fused arylcycloalkyls are those wherein the aryl thereof is phenyl and the cycloalkyl consists of about 5 to about 6 ring atoms. A fused arylcycloalkyl as a variable may be bonded through any atom of the ring system thereof capable of such. The fused arylcycloalkyl may be optionally substituted by one or more ring system substituent, wherein the "ring system substituent" is as defined herein. Representative fused arylcycloalkyl includes 1,2,3,4-tetrahydronaphthylene, and the like.

"Fused arylheterocyclenyl" means a fused aryl and heterocyclenyl as defined herein. Preferred fused arylheterocyclenyls are those wherein the aryl thereof is phenyl and the heterocyclenyl consists of about 5 to about 6 ring atoms. A fused arylheterocyclenyl as a variable may be bonded through any atom of the ring system thereof capable of such. The designation of the aza, oxa or thia as a prefix before heterocyclenyl portion of the fused arylheterocyclenyl define that at least a nitrogen, oxygen or sulfur atom is present respectively as a ring atom. The fused arylheterocyclenyl may be optionally substituted by one or more ring system substituent, wherein the "ring system substituent" is as defined herein. The nitrogen atom of a fused arylheterocyclenyl may be a basic nitrogen atom. The nitrogen or sulphur atom of the heterocyclenyl portion of the fused arylbeterocyclenyl may also be optionally oxidized to the corresponding N-oxide, S-oxide or S,S-dioxide. Representative fused arylheterocyclenyl include 3H-indolinyl, 1H-2-oxoquinolyl, 2H-1-oxoisoquinolyl, 1,2-dihydroquinolinyl, 3,4-dihydroquinolinyl, 1,2-dihydroisoquinolinyl, 3,4-dihydroisoquinolinyl, and the like.

"Fused arylheterocyclyl" means a fused aryl and heterocyclyl as defined herein. Preferred fused arylheterocyclyls are those wherein the aryl thereof is phenyl and the heterocyclyl consists of about 5 to about 6 ring atoms. A fused arylheterocyclyl as a variable may be bonded through any atom of the ring system thereof capable of such. The designation of the aza, oxa or thia as a prefix before heterocyclyl portion of the fused arylheterocyclyl define that at least a nitrogen, oxygen or sulfur atom is present respectively as a ring atom. The fused arylheterocyclyl may be optionally substituted by one or more ring system substituent, wherein the "ring system substituent" is as defined herein. The nitrogen atom of a fused arylheteroaryl may be a basic nitrogen atom. The nitrogen or sulphur atom of the heterocyclyl portion of the fused arylheterocyclyl may also be optionally oxidized to the corresponding N-oxide, S-oxide or S,S-dioxide. Representative preferred fused arylheterocyl ring systems include indolinyl, 1,2,3,4-tetrahydroisoquinoline, 1,2,3,4-tetrahydroquinoline, 1H-2,3-dihydroisoindol-2-yl, 2,3-dihydrobenz[f]isoindol-2-yl, 1,2,3,4-tetrahydrobenz[g]isoquinolin-2-yl, and the like.

"Aryloxy" means an aryl-O— group wherein the aryl group is as defined herein. Exemplary groups include phenoxy and 2-naphthyloxy.

"Aryloxycarbonyl" means an aryl-O—CO— group wherein the aryl group is as defined herein. Exemplary aryloxycarbonyl groups include phenoxycarbonyl and naphthoxycarbonyl.

"Arylsulfonyl" means an aryl-$SO_2$— group wherein the aryl group is as defined herein.

"Arylsulfonyl" means an aryl-SO— group wherein the aryl group is as defined herein.

"Arylthio" means an aryl-S— group wherein the aryl group is as herein described. Exemplary arylthio groups include phenylthio and naphthylthio.

"Basic nitrogen atom" means an $sp^2$ or $sp^3$ hybridized nitrogen atom having a non-bonded pair of electrons which is capable of being protonated. Examples of basic nitrogen atoms include optionally substituted imino, optionally substituted amino and optionally substituted amidino groups.

"Carboxy" means a HO(O)C— (carboxylic acid) group.

"Compounds of the invention", and equivalent expressions, are meant to embrace compounds of general formula (I) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

"Cycloalkyl" means a non-aromatic mono- or multicyclic ring system of about 3 to about 10 carbon atoms, preferably of about 5 to about 10 carbon atoms. Preferred ring sizes of rings of the ring system include about 5 to about 6 ring atoms. The cycloalkyl is optionally substituted with one or more "ring system substituents" which may be the same or different, and are as defined herein. Representative monocyclic cycloalkyl include cyclopentyl, cyclohexyl, cycloheptyl, and the like. Representative multicyclic cycloalkyl include 1-decalin, norbornyl, adamant-(1- or 2-)yl, and the like. Preferred ring system substituents for a cycloalkyl are amidino or $Y^1Y^2N$— as defined herein.

"Cycloalkenyl" means a non-aromatic mono- or multicyclic ring system of about 3 to about 10 carbon atoms, preferably of about 5 to about 10 carbon atoms, and which contains at least one carbon-carbon double bond. Preferred ring sizes of rings of the ring system include about 5 to about 6 ring atoms. The cycloalkenyl is optionally substituted with one or more "ring system substituents" which may be the same or different, and are as defined herein. Representative monocyclic cycloalkenyl include cyclopentenyl, cyclohexenyl, cycloheptenyl, and the like. A representative multicyclic cycloalkenyl is norbornylenyl. Preferred ring system substituents for a cycloalkyl are amidino or $Y^1Y^2N$— as defined herein "Derivative" means a chemically modified compound wherein the modification is considered routine by the ordinary skilled chemist, such as an ester or an amide of an acid, protecting groups, such as a benzyl group for an alcohol or thiol, and tert-butoxycarbonyl group for an amine.

"Di-alkylamino" means an (alkyl)(alkyl)-amino group wherein the alkyl groups are independent as herein defined.

"Diazo" means a bivalent —N=N— radical.

"Effective amount" is means an amount of a compound/composition according to the present invention effective in producing the desired therapeutic effect.

"Halo" means fluoro, chloro, bromo, or iodo. Preferred are fluoro, chloro or bromo, and more preferred are fluoro or chloro.

"Heteroaralkenyl" means an heteroaryl-alkenyl- group wherein the heteroaryl and alkenyl are as herein described. Preferred heteroaralkenyls contain a lower alkenyl moiety. An exemplary aralkenyl group is 4-pyridylvinyl, thienylethenyl, pyridylethenyl, imidazolylethenyl and pyrazinylethenyl.

"Heteroaralkyl" means a heteroaryl-alkyl- group wherein the heteroaryl and alkyl are as herein described. Preferred heteroaralkyls contain a lower alkyl moiety. Exemplary heteroaralkyl groups may contain thienylmethyl, pyridylmethyl, imidazolylmethyl and pyrazinylmethyl.

"Heteroaralkynyl" means an heteroaryl-alkynyl- group wherein the heteroaryl and alkynyl are as herein described.

Preferred heteroaralkynyls contain a lower alkynyl moiety. Exemplary heteroaralkynyl groups are pyrid-3-ylacetylenyl and quinolin-3-ylacetylenyl and 4-pyridylethynyl.

"Heteroaroyl" means an means an heteroaryl-CO— group wherein the heteroaryl group is as herein described. Exemplary groups include thiophenoyl, nicotinoyl, pyrrol-2-ylcarbonyl and 1- and 2-naphthoyl and pyridinoyl.

"Heteroaryl" means an aromatic monocyclic or multicyclic ring system of about 5 to about 14 carbon atoms, preferably about 5 to about 10 carbon atoms, in which one or more of the carbon atoms in the ring system is/are hetero element(s) other than carbon, for example nitrogen, oxygen or sulfur. Preferred ring sizes of rings of the ring system include about 5 to about 6 ring atoms. The "heteroaryl" may also be substituted by one or more "ring system substituents" which may be the same or different, and are as defined herein. The designation of the aza, oxa or thia as a prefix before heteroaryl define that at least a nitrogen, oxygen or sulfur atom is present respectively as a ring atom. A nitrogen atom of an heteroaryl may be a basic nitrogen atom and may also be optionally oxidized to the corresponding N-oxide. Representative heteroaryl and substituted heteroaryl groups include pyrazinyl, furanyl, thienyl, pyridyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyridazinyl, quinoxalinyl, phthalazinyl, imidazo[1,2-a]pyridine, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindole, 1,2,4-triazinyl and the like. Preferred heteroaryl groups include pyrazinyl, thienyl, pyridyl, pyrimidinyl, isoxazolyl and isothiazolyl.

"Heteroarylalkenyl" means a heteroaryl-alkenyl-group wherein the heteroaryl and alkenyl moieties are as described herein. Preferred heteroarylalkenyl groups contain a $C_{2-22}$ alkenyl moiety. Exemplary heteroarylalkenyl groups include pyridylpentenyl, pyridylhexenyl and pyridylheptenyl.

"Heteroarylalkynyl" means an aryl-alkynyl- group wherein the heteroaryl and alkynyl moiety are as herein described. Preferred heteroarylalkynyl groups contain a $C_{2-12}$ alkynyl moiety. Exemplary heteroarylalkynyl groups include 3-pyridyl-but-2-ynyl and pyridylpropynyl.

"Heteroaryldiazo" means an heteroaryl -azo- group wherein the heteroaryl and azo groups are as defined herein.

"Fused heteroarylcycloalkenyl" means a fused heteroaryl and cycloalkenyl as defined herein. Preferred fused heteroarylcycloalkenyls are those wherein the heteroaryl thereof is phenyl and the cycloalkenyl consists of about 5 to about 6 ring atoms. A fused heteroarylcycloalkenyl as a variable may be bonded through any atom of the ring system thereof capable of such. The designation of the aza, oxa or thia as a prefix before heteroaryl portion of the fused heteroarylcycloalkenyl define that at least a nitrogen, oxygen or sulfur atom is present respectively as a ring atom. The fused heteroarylcycloalkenyl may be optionally substituted by one or more ring system substituent, wherein the "ring system substituent" is as defined herein. The nitrogen atom of a fused heteroarylcycloalkenyl may be a basic nitrogen atom. The nitrogen atom of the heteroaryl portion of the fused heteroarylcycloalkenyl may also be optionally oxidized to the corresponding N-oxide. Representative fused heteroarylcycloalkenyl include 5,6-dihydroquinolyl, 5,6-dihydroisoquinolyl, 5,6-dibydroquinoxalinyl, 5,6-dihydroquinazolinyl, 4,5-dihydro-1H-benzimidazolyl, 4,5-dihydrobenzoxazolyl, and the like.

"Fused heteroarylcycloalkyl" means a fused heteroaryl and cycloalkyl as defined herein. Preferred fused heteroarylcycloalkyls are those wherein the heteroaryl thereof consists of about 5 to about 6 ring atoms and the cycloalkyl consists of about 5 to about 6 ring atoms. A fused heteroarylcycloalkyl as a variable may be bonded through any atom of the ring system thereof capable of such. The designation of the aza, oxa or thia as a prefix before heteroaryl portion of the fused heteroarylcycloalkyl define that at least a nitrogen, oxygen or sulfur atom is present respectively as a ring atom. The fused heteroarylcycloalkyl may be optionally substituted by one or more ring system substituent, wherein the "ring system substituent" is as defined herein. The nitrogen atom of a fused heteroarylcycloalkyl may be a basic nitrogen atom. The nitrogen atom of the heteroaryl portion of the fused heteroarylcycloalkyl may also be optionally oxidized to the corresponding N-oxide. Representative fused heteroarylcycloalkyl include 5,6,7,8-tetrahydroquinolinyl, 5,6,7,8-tetrahydroisoquinolyl, 5,6,7,8-tetrahydroquinoxalinyl, 5,6,7,8-tetrahydroquinazolyl, 4,5,6,7-tetrahydro-1H-benzimidazolyl, 4,5,6,7-tetrahydrobenzoxazolyl, 1H-4-oxa-1,5-diazanaphthalen-2-onyl, 1,3-dihydroimidizole-[4,5]-pyridin-2-onyl, and the like.

"Fused heteroarylheterocyclenyl" means a fused heteroaryl and heterocyclenyl as defined herein. Preferred fused heteroarylheterocyclenyls are those wherein the heteroaryl thereof consists of about 5 to about 6 ring atoms and the heterocyclenyl consists of about 5 to about 6 ring atoms. A fused heteroarylheterocyclenyl as a variable may be bonded through any atom of the ring system thereof capable of such. The designation of the aza, oxa or thia as a prefix before the heteroaryl or heterocyclenyl portion of the fused heteroarylheterocyclenyl define that at least a nitrogen, oxygen or sulfur atom is present respectively as a ring atom. The fused heteroarylheterocyclenyl may be optionally substituted by one or more ring system substituent, wherein the "ring system substituent" is as defined herein. The nitrogen atom of a fused heteroarylazaheterocyclenyl may be a basic nitrogen atom. The nitrogen or sulphur atom of the heteroaryl portion of the fused heteroarylheterocyclyl may also be optionally oxidized to the corresponding N-oxide. The nitrogen or sulphur atom of the heteroaryl or heterocyclyl portion of the fused heteroarylheterocyclyl may also be optionally oxidized to the corresponding N-oxide, S-oxide or S,S-dioxide. Representative fused heteroarylheterocyclenyl include 7,8-dihydro[1,7]naphthyridinyl, 1,2-dihydro[2,7]naphthyridinyl, 6,7-dihydro-3H-imidazo[4,5-c]pyridyl, 1,2-dihydro-1,5-naphthyridinyl, 1,2-dihydro-1,6-naphthyridinyl, 1,2-dihydro-1,7-naphthyridinyl, 1,2-dihydro-1,8-naphthyridinyl, 1,2-dihydro-2,6-naphthyridinyl, and the like.

"Fused heteroarylheterocyclyl" means a fused heteroaryl and heterocyclyl as defined herein. Preferred fused heteroarylheterocyclyls are those wherein the heteroaryl thereof consists of about 5 to about 6 ring atoms and the heterocyclyl consists of about 5 to about 6 ring atoms. A fused heteroarylheterocyclyl as a variable may be bonded through any atom of the ring system thereof capable of such. The designation of the aza, oxa or thia as a prefix before the heteroaryl or heterocyclyl portion of the fused heteroarylheterocyclyl define that at least a nitrogen, oxygen or sulfur atom is present respectively as a ring atom. The fused heteroarylheterocyclyl may be optionally substituted by one or more ring system substituent, wherein the "ring system substituent" is as defined herein. The nitrogen atom of a fused heteroarylheterocyclyl may be a basic nitrogen atom. The nitrogen or sulphur atom of the heteroaryl portion of the fused heteroarylheterocyclyl may also be optionally oxidized to the corresponding N-oxide. The nitrogen or sulphur atom of the heteroaryl or heterocyclyl portion of the fused heteroarylheterocyclyl may also be optionally oxidized to the corresponding N-oxide, S-oxide or S,S-dioxide. Representative fused heteroarylheterocyclyl include 2,3-dihydro-1H pyrrol[3,4-b]quinolin-2-yl, 1,2,3,4-tetrahydrobenz[b][1,7]naphthyridin-2-yl, 1,2,3,4-tetraliydrobenz[b][1,6]naphthyridin-2-yl, 1,2,3,4-tetrahydro-9H-pyrido[3,4-b]indol-2yl, 1,2,3,4-tetrahydro-9H-pyrido[4,3-b]indol-2yl, 2,3,-dihydro-1H-pyrrolo[3,4-b]indol-2-yl, 1H-2,3,4,5-tetrahydroazepino[3,4-b]indol-2-yl, 1H-2,3,4,5-tetrahydroazepino[4,3-b]indol-3-yl, 1H-2,3,4,5-tetrahydroazepino[4,5-b]indol-2 yl, 5,6,7,8-tetrahydro[1,7]napthyridinyl, 1,2,3,4-tetrhydro[2,7]naphthyridyl, 2,3-dihydro[1,4]dioxino[2,3-b]pyridyl, 2,3-dihydro[1,4]dioxino[2,3-b]pryidyl, 3,4-dihydro-2H-1-oxa[4,6]diazanaphthalenyl, 4,5,6,7-tetrahydro-3H-imidazo[4,5-c]pyridyl, 6,7-dihydro[5,8]diazanaphthalenyl, 1,2,3,4-tetrahydro[1,5]napthyridinyl, 1,2,3,4-tetrahydro[1,6]napthyridinyl, 1,2,3,4-tetrahydro[1,7]napthyridinyl, 1,2,3,4-tetrahydro[1,8]napthyridinyl, 1,2,3,4-tetrahydro[2,6]napthyridinyl, and the like.

"Heterocyclenyl" means a non-aromatic monocyclic or multicyclic hydrocarbon ring system of about 3 to about 10 carbon atoms, preferably about 5 to about 10 carbon atoms, in which one or more of the carbon atoms in the ring system is/are hetero element(s) other than carbon, for example nitrogen, oxygen or sulfur atoms, and which contains at least one carbon-carbon double bond or carbon-nitrogen double bond. Preferred ring sizes of rings of the ring system include about 5 to about 6 ring atoms. The designation of the aza, oxa or thia as a prefix before heterocyclenyl define that at least a nitrogen, oxygen or sulfur atom is present respectively as a ring atom. The heterocyclenyl may be optionally substituted by one or more ring system substituent, wherein the "ring system substituent" is as defined herein. The nitrogen atom of an heterocyclenyl may be a basic nitrogen atom. The nitrogen or sulphur atom of the heterocyclenyl may also be optionally oxidized to the corresponding N-oxide, S-oxide or S,S-dioxide. Representative monocyclic heterocyclenyl groups include 1,2,3,4-tetrahydrohydropyridine, 1,2-dihydropyridyl, 1,4-dihydropyridyl, 1,2,3,6-tetrahydropyridine, 1,4,5,6-tetrahydropyrimidine, 3,4-dihydro-2H-pyran, 2-pyrrolinyl, 3-pyrrolinyl, 2-imidazolinyl, 2-pyrazolinyl, tetrahydrothiophenyl, tetrahydrothiopyranyl, and the like. Preferred heterocyclenyl group substituents include amidino, halogen, hydroxy, alkoxycarbonylalkyl, carboxyalkyl or $Y^1Y^2N$— as defined herein.

"Heterocyclyl" means a non-aromatic saturated monocyclic or multicyclic ring system of about 3 to about 10 carbon atoms, preferably about 5 to about 10 carbon atoms, in which one or more of the carbon atoms in the ring system is/are hetero element(s) other than carbon, for example nitrogen, oxygen or sulfur. Preferred ring sizes of rings of the ring system include about 5 to about 6 ring atoms. The designation of the aza, oxa or thia as a prefix before heterocyclyl define that at least a nitrogen, oxygen or sulfur atom is present respectively as a ring atom. The heterocyclyl may be optionally substituted by one or more "ring system substituents" which may be the same or different, and are as defined herein. The nitrogen atom of an heterocyclyl may be a basic nitrogen atom. The nitrogen or sulphur atom of the heterocyclyl may also be optionally oxidized to the corresponding N-oxide, S-oxide or S,S-dioxide. Representative monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrabydrofuranyl, tetrahydrothiophenyl, tetrahydrothiopyranyl, and the like. Preferred heterocyclyl group substituents include amidino, halogen, hydroxy, alkoxycarbonylalkyl, carboxyalkyl or $Y^1Y^2N$— as defined herein.

"Hydrate" means a solvate wherein the solvent molecule(s) is/are $H_2O$.

"Hydroxyalkyl" means a HO-alkyl-group wherein alkyl is as herein defined. Preferred hydroxyalkyls contain lower alkyl. Exemplary hydroxyalkyl groups include hydroxymethyl and 2-hydroxyethyl.

"Modulate" means the ability of a compound to either directly (by binding to the receptor as a ligand) or indirectly (as a precursor for a ligand or an inducer which promotes production of a ligand from a precursor) induce expression of gene(s) maintained under hormone control, or to repress expression of gene (s) maintained under such control.

"N-oxide" means a moiety of the following structure

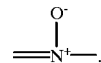

"Patient" includes both human and other mammals.

"Pharmaceutically acceptable cation" means those base addition salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable cations are well known in the art. For example, S. M Berge, et al. describe pharmaceutically acceptable salts in detail in J. Pharmaceutical Sciences, 1977, 66: p.1–19. Representative pharmaceutically acceptable cations include alkali or alkaline earth metal cations such as sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

"Pharmaceutically acceptable ester" means an ester which hydrolyzes in vivo and include that which breaks down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyates, acrylates and ethylsuccinates.

"Pharmaceutically acceptable prodrugs" as used herein means those prodrugs of the compounds of the present invention which are, within the scope of sound medical judgement, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in vivo to yield the parent compound of the above formula, for example by hydrolysis in blood. Functional groups which may be rapidly transformed, by metabolic cleavage, in vivo form a class of groups reactive with the carboxyl group of the compounds of this invention. They include, but are not limited to such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl-and triethysilyl), monoesters formed with dicarboxylic acids (such as succinyl), and the like. Because of the ease with which the metabolically cleavable groups of the compounds of this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: Design of Prodrugs, H. Bundgaard, ed., Elsevier, 1985; Methods in Enzyrnology, K. Widder et al, Ed., Academic Press, 42, p.309–396, 1985; A Textbook of Drug Design and Developement, Krogsgaard-Larsen and H. Bundgaard, ed., Chapter 5; "Design and Applications of Prodrugs" p.113–191, 1991; Advanced Drug Delivery Reviews, H. Bundgard, 8, p.1–38, 1992; Journal of Pharmaceutical Sciences, 77, p. 285, 1988; Chem. Pharm. Bull., N. Nakeya et al, 32, p. 692, 1984; Prodrugs as Novel Delivery Systems, T. Higuchi and V. Stella, Vol. 14 of the A.C.S. Symposium Series, and Bioreversible Carriers in Drug Design, Edward B. Roche, ed., American Pharmaceutical Association and Pergamon Press, 1987, which are incorporated herein by reference.

"Optionally substituted tetrazolyl" means a group of formula

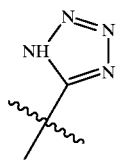

wherein the hydrogen atom thereof may be substituted by alkyl, carboxyalkyl or carbalkoxyalkyl.

"Ring system substituents" mean substituents attached to aromatic or non-aromatic ring systems inclusive of hydrogen, alkyl, aryl, heteroaryl, aralkyl, heteroaralkyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, aryldiazo, heteroaryldiazo, amidino, $Y^1Y^2N$—, $Y^1Y^2N$-alkyl-, $Y^1Y^2NCO$— or $Y^1Y^2N$ $SO_2$—, wherein $Y^1$ and $Y^2$ are independently hydrogen, optionally substituted alkyl, optionally substituted aryl, optionally substituted aralkyl or optionally substituted heteroaralkyl, or for where the substituent is $Y^1Y^2N$—, $Y^1Y^2N$-alkyl-, then one of $Y^1$ and $Y^2$ may be acyl or aroyl as defined herein and the other of $Y^1$ and $Y^2$ is as defined previously, or for where the substituent is $Y^1Y^2NCO$— or $Y^1Y^2NSO_2$, $Y^1$ and $Y^2$ may also be taken together with the N atom through which $Y^1$ and $Y^2$ are linked to form a 4 to 7 membered heterocyclyl or heterocyclenyl. When a ring system is saturated or partially saturated, the "ring system substituents" further include, methylene ($H_2C$=), oxo (O=), thioxo (S=). Ring system substituents encompassing a basic nitrogen atom include optionally substituted amidino, optionally substituted imino, and optionally substituted amine groups. Preferred ring system substituents include, halo, alkoxy, $Y^1Y^2N$-alkyl-, $Y^1Y^2NCO$—, and oxo (O=).

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include ethanolates, methanolates, and the like.

"$Y^1Y^2N$—" means a substituted or unsubstituted amino group, wherein $Y^1$ and $Y^2$ are as herein described. Exemplary groups include amino ($H_2N$—), methylamino, dimethylamino, diethylamino, pyrrolidine, piperidine, benzylamino, or phenethylamino.

"$Y^1Y^2NCO$—" means a substituted or unsubstituted carbamoyl group, wherein $Y^1$ and $Y^2$ are as herein described. Exemplary groups are carbamoyl ($H_2NCO$—) and dimethylaminocarbamoyl ($Me_2NCO$—).

"$Y^1Y^2NSO_2$—" means a substituted or unsubstituted sulfamoyl group, wherein $Y^1$ and $Y^2$ are as herein described. Exemplary groups are aminosulfamoyl ($H_2NSO_2$—) and dimethylaminosulfamoyl ($Me_2NSO_2$—).

In a specific embodiment, the term "about" or "approximately" means within 20%, preferably within 10%, and more preferably within 5% of a given value or range.

PREFERRED EMBODIMENTS

A preferred embodiment of the invention is a method for treating a disease state in a patient, associated with a detrimental excess of Factor Xa activity, comprising administering to said patient a pharmaceutically effective amount of the compound of formula I, or a pharmaceutically acceptable salt thereof.

Another preferred aspect of the invention is the compound of formula I wherein $R^1$ is a group of formula

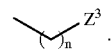

Another preferred aspect of the invention is the compound of formula I wherein $R^2$ is hydrogen, —$CO_2R^5$, —$C(O)R^5$, —$CH_2OR^6$ or —$CH_2SR^6$.

Another preferred aspect of the invention is the compound of formula I wherein $R^2$ is hydrogen, —$CO_2R^5$, —$CH_2OR^6$ or —$CH_2SR^6$; more preferred is wherein $R^2$ is hydrogen, —$CO_2R^5$ or —$CH_2OR^6$.

Another preferred aspect of the invention is the compound of formula I wherein $R^2$ is —$CO_2R^5$ and $R^5$ is lower alkyl.

Another preferred aspect of the invention is the compound of formula I wherein $R^2$ is —$CH_2OR^6$ or —$CH_2SR^6$ and $R^6$ is hydrogen or lower alkyl.

Another preferred aspect of the invention is the compound of formula I wherein $R^3$ is lower alkyl, $R^6O$(lower alkyl)-, or a group of formula

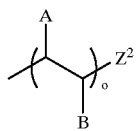

Another preferred aspect of the invention is the compound of formula I wherein $R^3$ is hydrogen, alkyl, $Z^1$-alkyl, or a group of formula

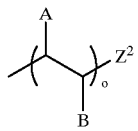

Another preferred aspect of the invention is the compound of formula I wherein $R^4$ is optionally substituted cycloalkyl, optionally substituted cycloalkenyl, optionally substituted heteroaryl, optionally substituted fused arylcycloalkyl, optionally substituted fused arylcycloalkyl, optionally substituted fused arylcycloalkenyl, optionally substituted fused arylheteroaryl, optionally substituted fused heteroarylaryl, optionally substituted fused heteroarylcycloalkyl, optionally substituted fused heteroarylcycloalkenyl, optionally substituted fused heteroarylheterocyclyl, optionally substituted fused heteroarylheterocyclenyl.

Another preferred aspect of the invention is the compound of formula I wherein $R^4$ is optionally substituted cycloalkyl, optionally substituted heterocyclyl, optionally substituted aryl, optionally substituted heteroaryl, optionally substituted aralkyl or optionally substituted aralkynyl.

Another preferred aspect of the invention is the compound of formula I wherein $R^4$ is optionally substituted phenyl, optionally substituted naphthyl, or optionally substituted heteroaryl.

Another preferred aspect of the invention is the compound of formula I wherein $R^4$ is phenyl, biphenyl, naphthyl, phenyl or heterobiphenyl.

Another preferred aspect of the invention is the compound of formula I wherein $R^4$ is optionally substituted (phenyl substituted phenyl), optionally substituted (heteroaryl substituted phenyl), optionally substituted (phenyl substituted heteroaryl) or optionally substituted (heteroaryl substituted heteroaryl), (wherein the term "optionally substituted" before the term in the parenthesis, denote that the phenyl or heteroaryl portions thereof could be further substituted as noted per their definitions).

Another preferred aspect of the invention is the compound of formula I wherein $R^5$ is lower alkyl.

Another preferred aspect of the invention is the compound of formula I wherein $R^6$ is hydrogen or lower alkyl.

Another preferred aspect of the invention is the compound of formula I wherein $R^6$ is hydrogen or lower alkyl.

Another preferred aspect of the invention is the compound of formula I wherein $R^7$ is hydrogen.

Another preferred aspect of the invention is the compound of formula I wherein A and B together are a direct bond.

Another preferred aspect of the invention is the compound of formula I wherein C and D together are a direct bond.

Another preferred aspect of the invention is the compound of formula I wherein A and B are hydrogen.

Another preferred aspect of the invention is the compound of formula I wherein C and D are hydrogen.

Another preferred aspect of the invention is the compound of formula I wherein $Z^1$ is $R^6O$—.

Another preferred aspect of the invention is the compound of formula I wherein $Z^3$ is optionally substituted azaheteroaryl, optionally substituted azaheterocyclyl, optionally substituted heterocyclenyl, optionally substituted fused azaheteroarylcycloalkyl, optionally substituted fused azaheteroarylcycloalkenyl, optionally substituted fused azaheteroarylheterocyclyl, optionally substituted fused azaheteroarylheterocyclenyl, optionally substituted fused azaheteroarylazaheterocyclyl, optionally substituted fused azaheteroarylazaheterocyclenyl.

Another preferred aspect of the invention is the compound of formula I wherein $Z^1$ is optionally substituted dihydropyridine, optionally substituted tetrahydropyridine, or optionally substituted piperidine.

Another preferred aspect of the invention is the compound of formula I wherein $Z^3$ is substituted by, at least, $Y^1Y^2N$— or $Y^1Y^2N$-alkyl-.

Another preferred aspect of the invention is the compound of formula I wherein $Z^3$ is substituted by a moiety of the formula

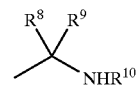

wherein $R^{10}$ is hydrogen, HO—, or $R^{12}O_2C$—, and $R^8$ and $R^9$ are hydrogen or together are $=NR^{11}$, and $R^{11}$ is selected from hydrogen, $R^{12}O_2C$—, $R^{12}O$—, HO—, $R^{12}C(O)$—, HCO—, cyano, optionally substituted lower alkyl, nitro or $Y^{1a}Y^{2a}N$—; wherein $R^{12}$ is alkyl, optionally substituted aralkyl, or optionally substituted heteroaralkyl, and $Y^{1a}$ and $Y^{2a}$ are independently hydrogen or alkyl.

Another preferred aspect of the invention is the compound of formula I wherein $Z^3$ is substituted by, at least, an amidino group.

Another preferred aspect of the invention is the compound of formula I wherein $Z^3$ is substituted by, at least, an amidino group of the formula

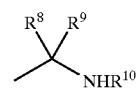

wherein $R^8$ and $R^9$ together are $=NR^{11}$, and $R^{11}$ is hydrogen.

Another preferred aspect of the invention is the compound of formula I wherein $Z^3$ is substituted azaheterocyclyl or substituted azaheterocyclenyl; and at least one of the ring system substituents of the substituted azaheterocyclyl or substituted azaheterocyclenyl is an amidino group.

Another preferred aspect of the invention is the compound of formula I wherein $Z^3$ is substituted by, at least, an amidino group in the meta or para position of the ring system of $Z^3$, relative to the position of attachment of $Z^3$ to the rest of the molecule.

Another preferred aspect of the invention is the compound of fornula I wherein $Z^3$ is substituted by a moiety of the formula

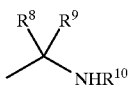

wherein $R^8$ and $R^9$ together are hydrogen.

Another preferred aspect of the invention is the compound of formula I wherein $Z^3$ is substituted by a moiety of the formula

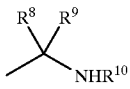

wherein $R^8$ and $R^9$ are $=NR^{11}$, and $R^{11}$ is HO—.

Another preferred aspect of the invention is the compound of formula I wherein $Z^3$ is substituted by a moiety of the formula

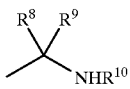

wherein $R^{10}$ is hydrogen.

Another preferred aspect of the invention is the compound of formula I wherein $Z^3$ is substituted by a moiety of the formula

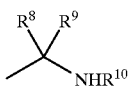

wherein $R^{10}$ is HO—.

Another preferred aspect of the invention is the compound of formula I wherein $Z^3$ is substituted by a moiety of the formula

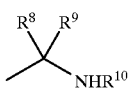

wherein $R^{10}$ is $R^{12}O_2C$—.

Another preferred aspect of the invention is the compound of formula I wherein $Z^3$ is substituted by a moiety of the formula

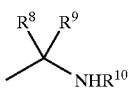

wherein $R^8$ and $R^9$ are $=NR^{11}$, and $R^{11}$ is selected from hydrogen, $R^{12}O_2C$—, $R^{12}O$—, HO—, $R^{12}C(O)$—, wherein $R^{12}$ is lower alkyl.

Another preferred aspect of the invention is the compound of formula I wherein m is 1.

Another preferred aspect of the invention is the compound of formula I wherein o is 1.

Another preferred aspect of the invention is the compound of formula I wherein n is 1 or 3.

Another preferred aspect of the invention is the compound of formula I wherein p is 1 or 3.

Another preferred aspect of the invention is the compound of formula I wherein p is 1.

Another preferred aspect of the invention is the compound of formula I wherein A and B are hydrogen, and o is 1.

Another preferred aspect of the invention is the compound of formula I wherein A, B, C, D, $R^7$ and $R^{10}$ are hydrogen.

Species according to the invention are selected from the following:

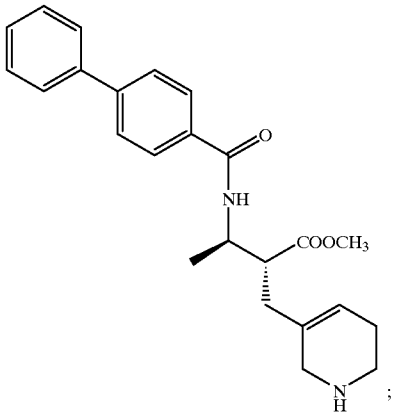

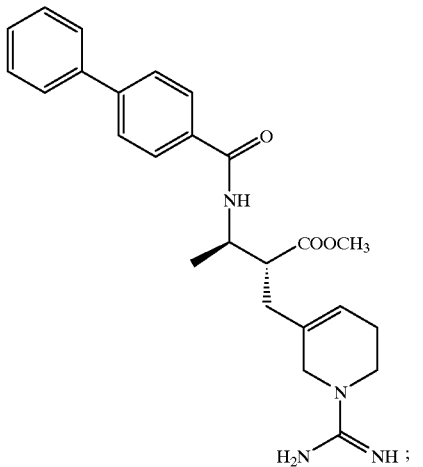

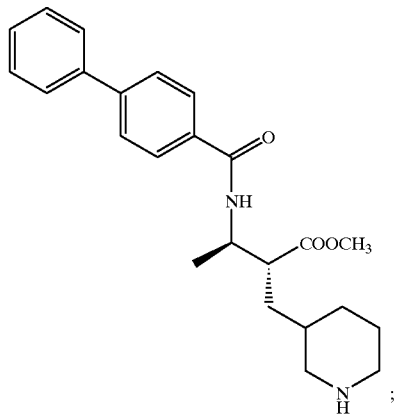

-continued
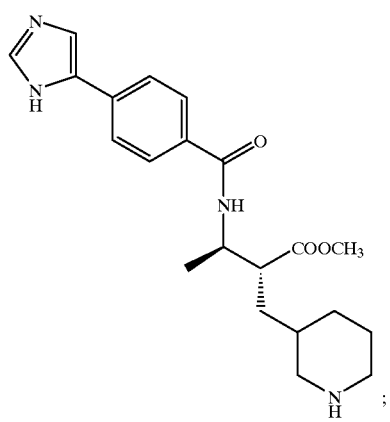
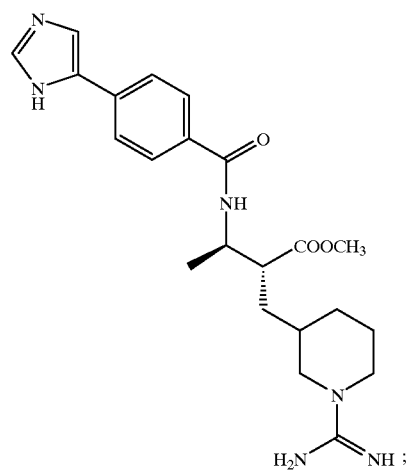
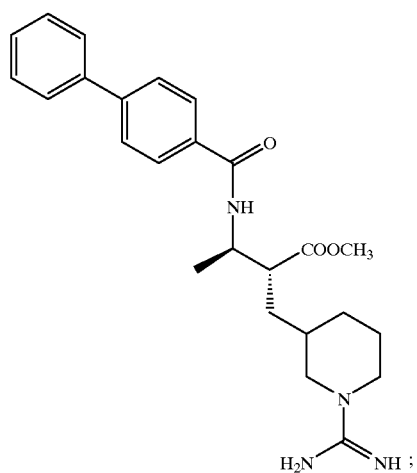
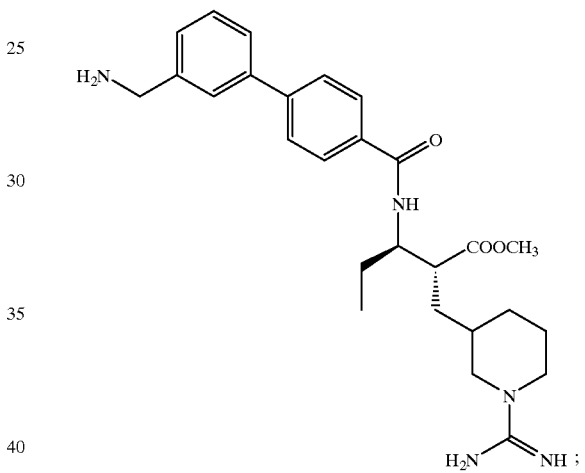
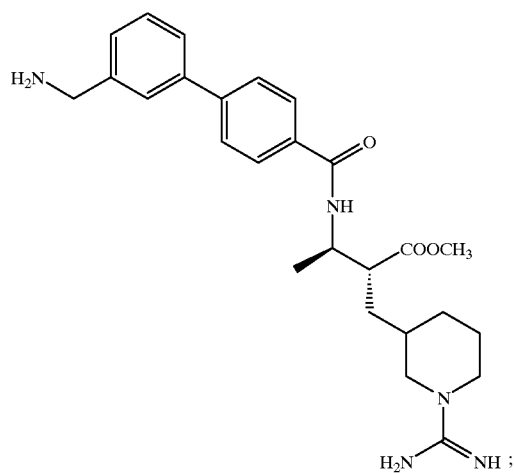
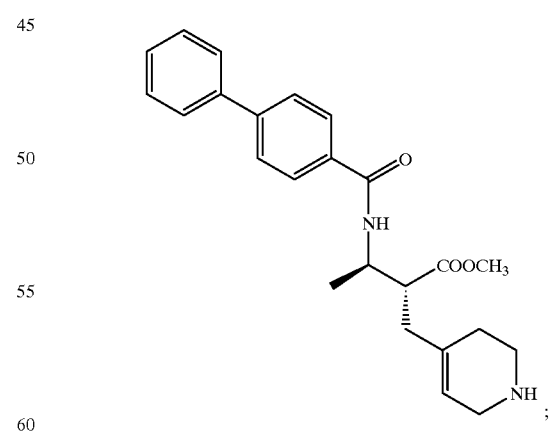

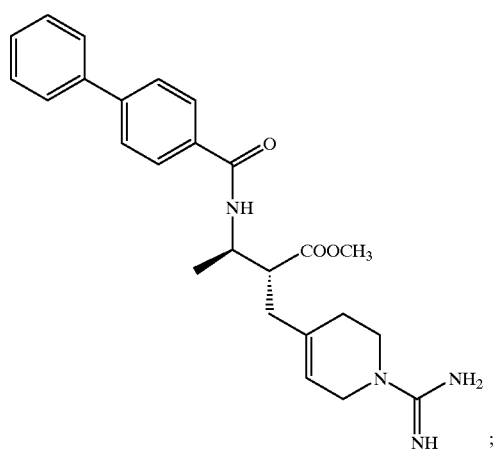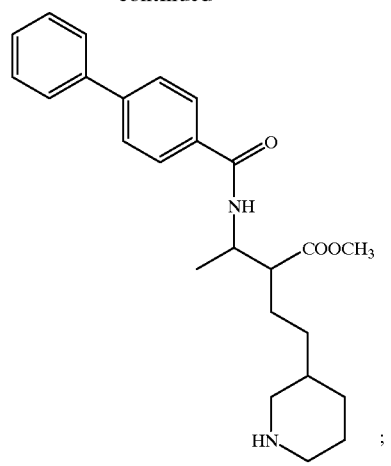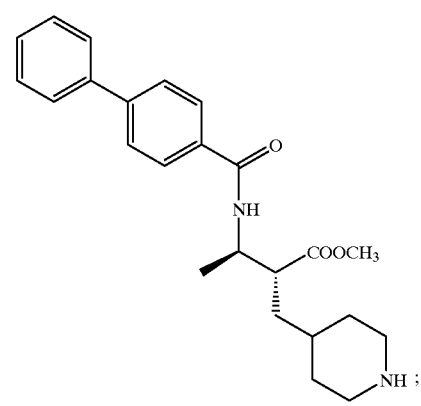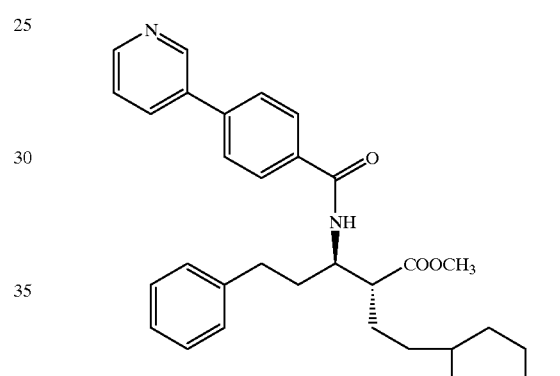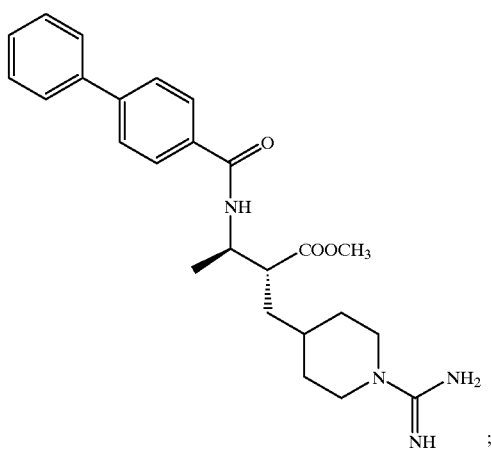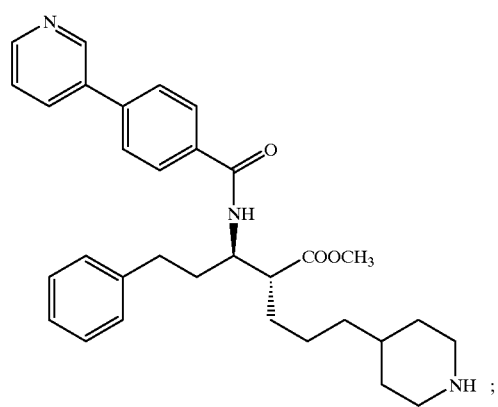

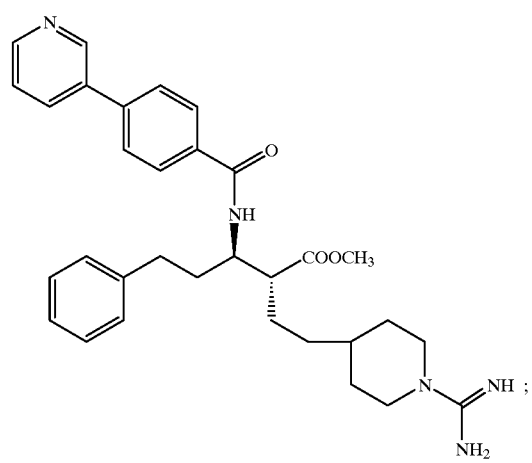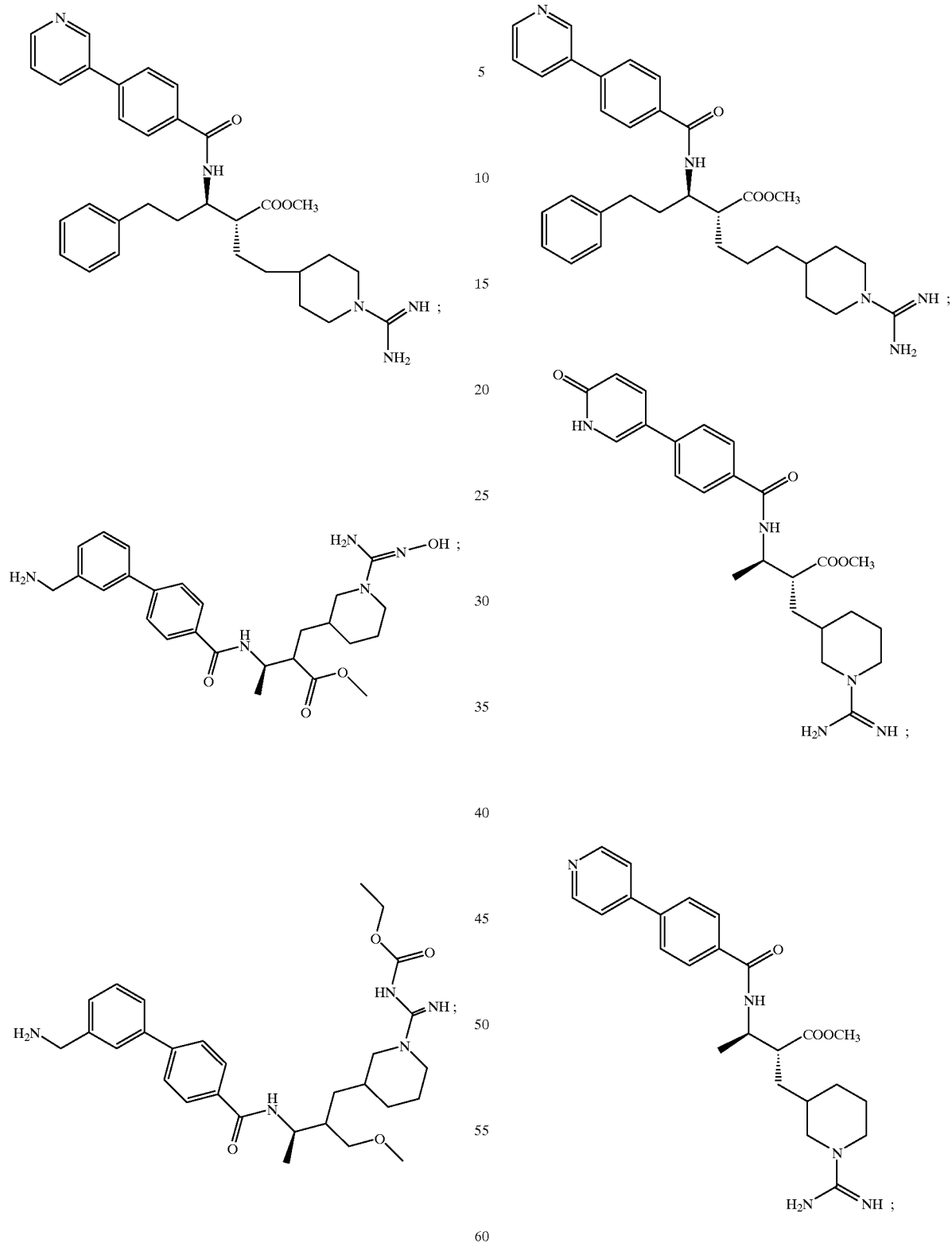

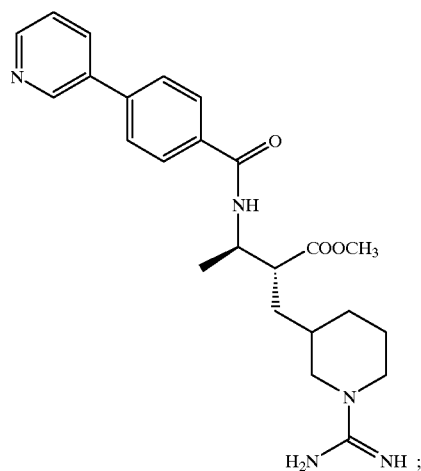
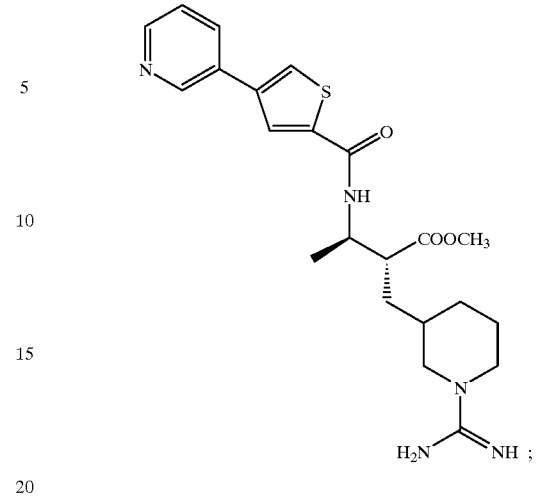
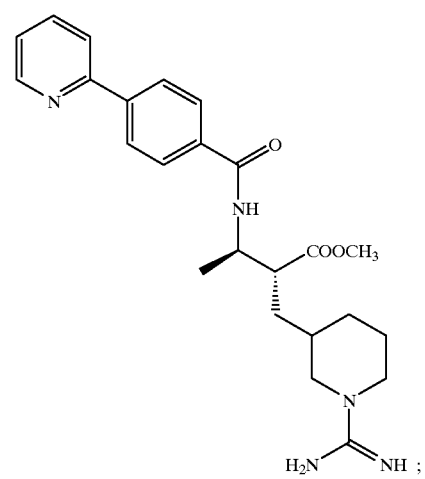
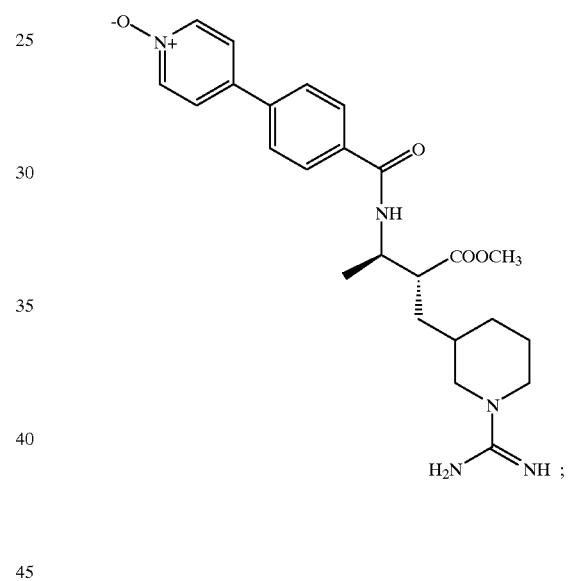
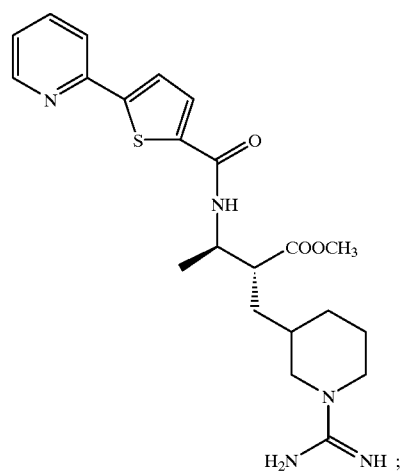
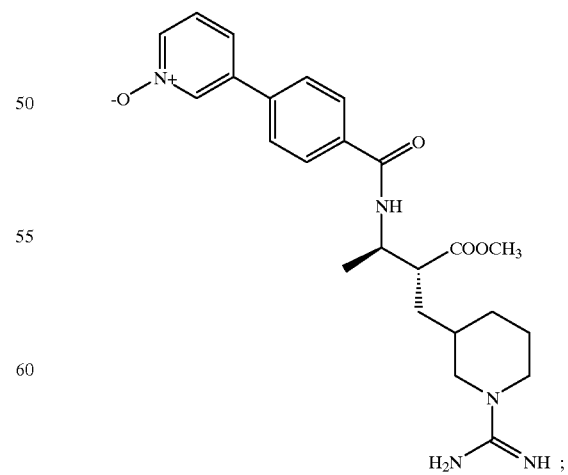

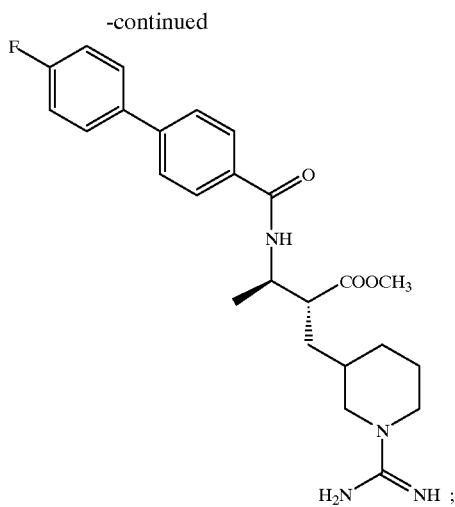
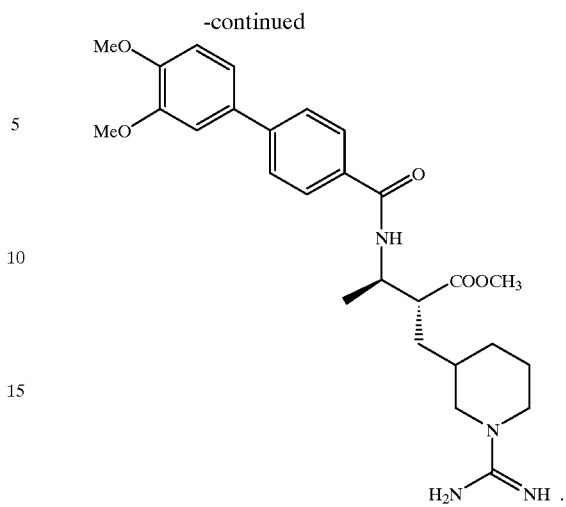
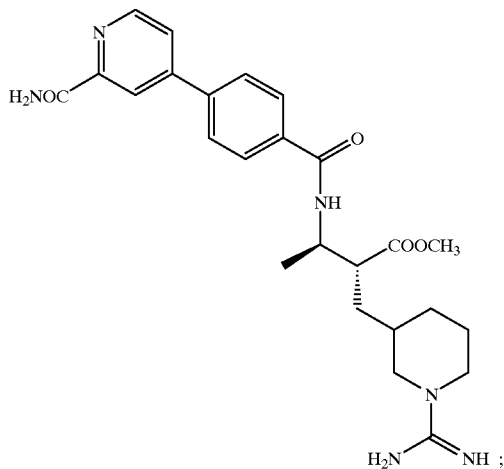
Preferred species are selected from the following:
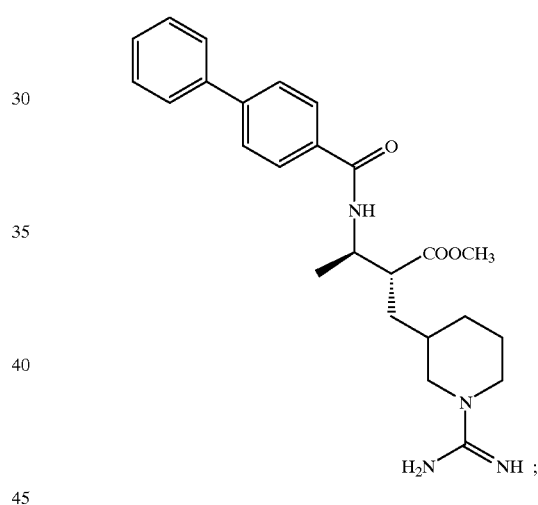
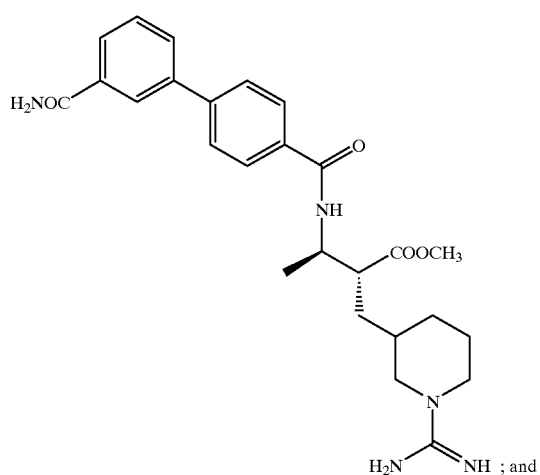
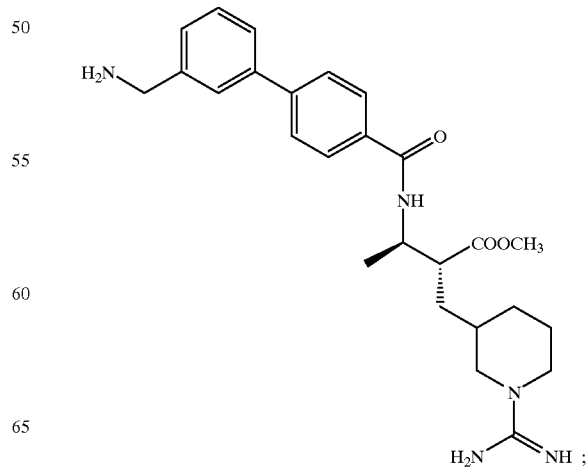

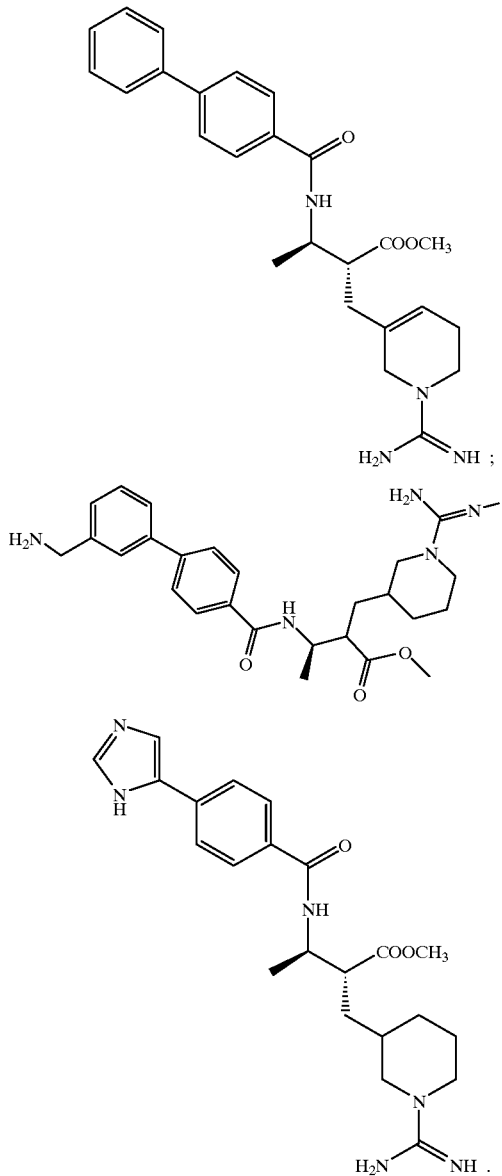

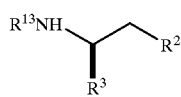

This invention also encompasses all combinations of preferred aspects of the invention noted herein.

Compounds of Formula I may be prepared by the application or adaptation of known methods, by which is meant methods used heretofore or described in the literature, or by methods according to this invention herein.

Compounds of formula (III)

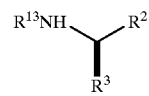

(III)

wherein $R^2$ and $R^3$ are hereinbefore defined and $R^{13}$ is an appropriate amine protecting group, may be prepared by conversion of the corresponding amine protected α-amino compound of formula (II)

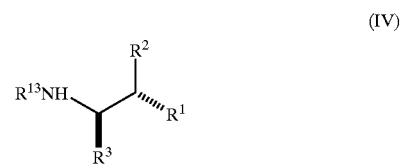

(II)

wherein $R^3$ and $R^{13}$ are as hereinbefore defined, $R^2$ is $COOR^5$, and $R^5$ is hydrogen, by a method known as the Arndt-Eistert synthesis (See J March, Advanced Organic Chemistry, 3rd ed., Wiley Intersciences; Meier et al., Angew. Chem. Int. Ed. Engl. 14, p.32–43, 1975). For example, by converting $R^2$ to the acyl halide, and then reacting it with diazomethane, or the like, in an appropriate solvent to form the diazoketone derivative. Treatment of the diazoketone derivative with water (or alcohol) and silveroxide, or the like, affords the compound of formula (III).

The compound of formula (IV)

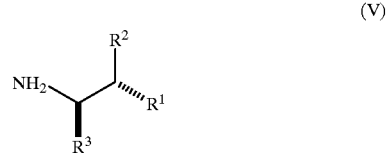

(IV)

wherein $R^1$, $R^3$ and $R^{13}$ are as hereinbefore defined, $R^2$ is $CO_2R^5$, wherein $R^5$ is lower alkyl, may be prepared by alkylation of the compound (III) at the α-position by deprotonating at the α-position with an appropriate base, followed by alkylation with an appropriate alkyl halide $R^1$—X, wherein $R^1$ is as hereinbefore defined.

The compound of formula (V)

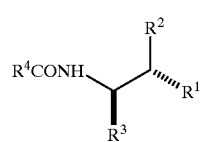

(V)

wherein $R^1$, $R^2$, $R^3$ are as hereinbefore defined, may be synthesized by selectively removing the amino protecting group $R^{13}$ of the compound of formula (IV) using known procedures for deprotecting amino groups. For example, wherein $R^{13}$ is an acid labile amino protecting group (e.g. tert-butoxycarbonyl (BOC)) the amino protecting group may be removed by treatment with acid.

The amide compound of formula (VII)

(VII)

$$R^4CONH\underset{R^3}{\overset{R^2}{\diagdown}}R^1$$

wherein $R^1$, $R^2$, $R^3$ and $R^4$ are as hereinbefore defined, may be synthesized by reacting a compound of formula (V) with a compound of formula (VI)

$$R^4\text{—COOH} \qquad (VI)$$

wherein $R^4$ is as hereinbefore defined, under standard peptide coupling procedures such as treatment with a carbodiimide, for example dicyclohexylcarbodiimide, or 2-(1H-benzotriazol-1-yl)-1,1,3,3-tetramethyluronium tetrafluoroborate, in the presence of a base, for example, triethylamine, in an inert solvent such as dichloromethane or tetrahydrofuran and at a temperature at about room temperature.

The compound of formula (VII) wherein $R^2$, $R^3$ and $R^4$ are as hereinbefore defined; $R^1$ is a group of formula

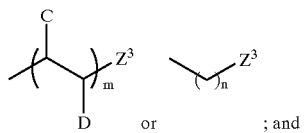

$Z^3$ is substituted aryl, substituted cycloalkyl, substituted cycloalkenyl, optionally substituted heteroaryl, optionally substituted heterocyclyl, optionally substituted heterocyclenyl, substituted fused arylcycloalkyl, substituted fused arylcycloalkenyl, optionally substituted fused heteroarylcycloalkyl, optionally substituted fused heteroarylcycloalkenyl, optionally substituted fused heteroarylheterocyclyl, optionally substituted fused heteroarylheterocyclenyl, wherein at least one of the ring system substituents contains at least one unprotected nitrogen atom, or an unprotected nitrogen atom is incorporated in the ring system of the heteroaryl, heterocyclyl or heterocyclenyl moiety, may be synthesized by selectively removing the amino protecting group from a compound of formula (VII) wherein $R^1$, $R^2$, $R^3$ and $R^4$ are as hereinbefore defined and wherein at least one of the ring system substituents of $Z^3$ contains at least one amine protected nitrogen atom, or an amine protected nitrogen atom is incorporated in the ring system of the heteroaryl, heterocyclyl or heterocyclenyl moiety, using known procedures for deprotecting amino groups. For example, wherein the amino protecting group is a hydrogenation labile amine protecting group, the amino protecting group may be removed by hydrogenation. A preferred hydrogenation labile amine protecting group is benzyloxycarbonyl (CBZ).

The compound of formula (VIII) wherein $R^2$, $R^3$ and $R^4$ are as hereinbefore defined; $R^1$ is a group of formula

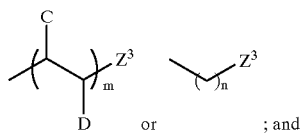

$Z^3$ is substituted azaheteroaryl, substituted azaheterocyclyl, substituted azaheterocyclenyl, substituted fused azaheteroarylcycloalkyl, substituted fused azaheteroarylcycloalkenyl, substituted fused azaheteroarylheterocyclyl, substituted fused azaheteroarylheterocyclenyl, substituted fused azaheteroarylazaheterocyclyl, substituted fused azaheteroarylazaheterocyclenyl wherein at least one nitrogen atom incorporated in the ring system is substituted by

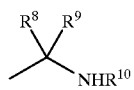

wherein $R^8$, $R^9$ are $=NR^{11}$, and $R^{10}$ and $R^{11}$ is as herein before defined, may be synthesized by reacting a compound of formula (VII) wherein $Z^3$ is substituted aryl, substituted cycloalkyl, substituted cycloalkenyl, optionally substituted heteroaryl, optionally substituted heterocyclyl, optionally substituted heterocyclenyl, substituted fused arylcycloalkyl, substituted fused arylcycloalkenyl, optionally substituted fused heteroarylcycloalkyl, optionally substituted fused heteroarylcycloalkenyl, optionally substituted fused heteroarylheterocyclyl, optionally substituted fused heteroarylheterocyclenyl, wherein at least one of the ring system nitrogen atoms is a basic nitrogen atom, with a compound of formula (IX)

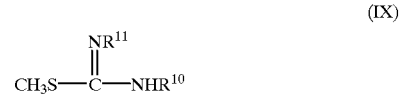

wherein $R^{10}$ and $R^{11}$ is as herein before defined, in the presence of mercuric chloride, an amine base, and an appropriate solvent, at a temperature of between about 0° C. and about room temperature.

In the reactions described, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Green and P. G. M. Wuts in "Protective Groups in Organic Chemistry" John Wiley and Sons, 1991.

It will be apparent to those skilled in the art that certain compounds of formula I can exhibit isomerism, for example geometrical isomerism, e.g., E or Z isomerism, and optical isomerism, e.g., R or S configurations. Geometrical isomers include the cis and trans forms of compounds of the invention having alkenyl moieties. Individual geometrical isomers and stereoisomers within formula I, and their mixtures, are within the scope of the invention.

Such isomers can be separated from their mixtures, by the application or adaptation of known methods, for example chromatographic techniques and recrystallization techniques, or they are separately prepared from the appropriate isomers of their intermediates, for example by the application or adaptation of methods described herein.

A compound of formula I including an heteroaryl group containing one or more nitrogen ring atoms, preferably imine (=N—), may be converted to the corresponding compound wherein one or more nitrogen ring atom of the heteroaryl moiety is oxidized to an N-oxide, preferably by reacting with a peracid, for example peracetic acid in acetic acid or m-chloroperoxybenzoic acid in an inert solvent such as dichloromethane, at a temperature from about room temperature to reflux, preferably at elevated temperature.

The compounds of the present invention are useful in the form of the free base or acid or in the form of a pharmaceutically acceptable salt thereof. All forms are within the scope of the invention.

Where the compound of the present invention is substituted with a basic moiety, acid addition salts are formed and are simply a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects on Factor Xa inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesufonic acid, ethanesulfonic acid, benzenesulfonic acid, p-toluenesulfonic acid, cyclohexylsulfamic acid, quinic acid, and the like. The corresponding acid addition salts comprise the following: hydrohalides, e.g. hydrochloride and hydrobromide, sulfate, phosphate, nitrate, sulfamate, acetate, citrate, lactate, tartarate, malonate, oxalate, salicylate, propionate, succinate, fumarate, maleate, methylene-bis-B-hydroxynaphthoates, gentisates, mesylates, isethionates and di-p-toluoyltartratesmethanesulfonate, ethanesulfonate, benzenesulfonate, p-toluenesulfonate, cyclohexylsulfamate and quinate, respectively.

According to a further feature of the invention, acid addition salts of the compounds of this invention are prepared by reaction of the free base with the appropriate acid, by the application or adaptation of known methods. For example, the acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For example, parent compounds of the invention can be regenerated from their acid addition salts by treatment with an alkali, e.g. aqueous sodium bicarbonate solution or aqueous ammonia solution.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the animal organism in pharmaceutical doses of the salts, so that the beneficial inhibitory effects on Factor Xa inherent in the free acid are not vitiated by side effects ascribable to the cations. Pharmaceutically acceptable salts, including for example alkali and alkaline earth metal salts, within the scope of the invention are those derived from the following bases: sodium hydride, sodium hydroxide, potassium hydroxide, calcium hydroxide, aluminum hydroxide, lithium hydroxide, magnesium hydroxide, zinc hydroxide, ammonia, ethylenediamine, N-methyl-glucamine, lysine, arginine, omithine, choline, N,N'-dibenzylethylenediamine, chloroprocaine, diethanolamine, procaine, N-benzylphenethylamine, diethylamine, piperazine, tris (hydroxymethyl)-aminomethane, tetramethylammonium hydroxide, and the like.

Metal salts of compounds of the present invention may be obtained by contacting a hydride, hydroxide, carbonate or similar reactive compound of the chosen metal in an aqueous or organic solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds of the present invention may be obtained by contacting an amine in an aqueous or organic solvent with the free acid form of the compound. Suitable aqueous solvents include water and mixtures of water with alcohols such as methanol or ethanol, ethers such as tetrahydrofuran, nitriles such as acetonitrile, or ketones such as acetone. Amino acid salts may be similarly prepared.

The base addition salts of the compounds of this invention can be regenerated from the salts by the application or adaptation of known methods. For example, parent compounds of the invention can be regenerated from their base addition salts by treatment with an acid, e.g. hydrochloric acid.

Pharmaceutically acceptable salts also include quaternary lower alkyl ammonium salts. The quaternary salts are prepared by the exhaustive alkylation of basic nitrogen atoms in compounds, including nonaromatic and aromatic basic nitrogen atoms, according to the invention, i.e., alkylating the non-bonded pair of electrons of the nitrogen moieties with an alkylating agent such as methylhalide, particularly methyl

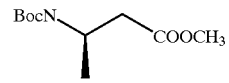

To a solution of N-α-Boc-D-Alanine (38 mmol) in 80 mL of dry tetrahydrofuran is added N-methyl morpholine (38 mmol) in a single portion, followed by isobutyl chloroformate (38 mmol) in a similar fashion, at −20° C. The reaction mixture is stirred for 10 minutes at −20° C. and filtered into a preformed ethereal solution of diazomethane (~70 mmol) at 0° C. The resulting solution is allowed to stand at 0° C. for 20 minutes. Excess diazomethane is decomposed by the dropwise addition of glacial acetic acid and solvents are removed in vacuo.

The resulting oil is dissolved in 150 mL of dry methanol. A solution of silver benzoate (8 mmol) in 17 mL of triethylamine is slowly added with stirring, at room temperature. The resulting black reaction mixture is stirred for 45 minutes at room temperature. Methanol is removed in vacuo and the residue taken up in 700 mL of ethyl acetate. The mixture is filtered through celite and washed sequentially with saturated sodium bicarbonate (3×150 mL), water (1×150 mL), 1N potassium bisulfate (3×150 mL) and brine (1×150 mL). The organic layer is dried over magnesium sulfate, filtered, concentrated in vacuo, and purified by flash chromatography (3:1 hexanes:ethyl acetate).

Intermediate Example 2
N-tert-butoxycarbonylamino-3-(R)-ethyl β-alanine methyl ester

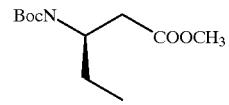

The compound of intermediate Example 2 is prepared in the same fashion as the compound of Intermediate Example 1 substituting 2-(R)-amino-butanoic acid for N-α-Boc-D-Alanine.

Intermediate Example 3

N-Benzyloxycarbonyl-3-iodomethyl-1,2,5,6-tetrahydropyridine iodide, or dimethyl sulfate. Quaternarization results in the nitrogen moiety becoming positively charged and having a negative counter ion associated therewith.

As will be self-evident to those skilled in the art, some of the compounds of this invention do not form stable salts. However, acid addition salts are more likely to be formed by compounds of this invention having a nitrogen-containing heteroaryl group and/or wherein the compounds contain an amino group as a substituent. Preferable acid addition salts of the compounds of the invention are those wherein there is not an acid labile group.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

The starting materials and intermediates are prepared by the application or adaptation of known methods, for example methods as described in the Reference Examples or their obvious chemical equivalents, or by methods according to this invention.

The present invention is further exemplified but not limited by the following illustrative examples which illustrate the preparation of the compounds according to the invention.

In the nuclear magnetic resonance spectra (NMR) the chemical shifts are expressed in ppm relative to tetramethylsilane. Abbreviations have the following significance: s=singlet; d=doublet; t=triplet; m=multiplet; dd=doublet of doublets; ddd=doublet of doublets of doublets; dt=doublet of triplets, b=broad.

EXPERIMENTAL

"Work up" in the experimental means drying over magnesium sulfate, filtering, and concentrating in vacuo.

Intermediate Example 1

N-tert-butoxycarbonylamino-3-(R)-methyl β-alanine methyl ester

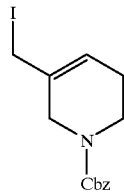

(A) To a solution of 3-pyridyl carbinol (100 mmol) in 30 mL of ethanol is added benzyl bromide (110 mmol) dropwise via addition funnel at room temperature. Stirring is continued for 2 hours at room temperature and solvents are removed in vacuo. The residue is taken up into acetonitrile (100 mL) and washed with hexanes (3×100 mL). The acetonitrile layer is concentrated in vacuo and dried under vacuum to provide N-benzyl-3-pyridyl carbinol bromide.

(B) To this material (54 mmol) in 250 mL of ethanol is added sodium borohydride (161 mmol) portionwise at 0° C. over 10 minutes. Stirring is continued for 90 minutes at 0° C. Ethanol is evaporated in vacuo and the residue partitioned between methylene chloride (600 mL) and saturated sodium bicarbonate solution (150 mL). The organic layer is further washed with saturated sodium bicarbonate (3×100 mL) and brine. The organic layer is worked up and purified by preparative chromatography using 1:1 ethyl acetate:hexanes to give N-benzyl-3-hydroxymethyl-1,2,5,6-tetrahydropyridine. $^1$H NMR (CDCl$_3$) δ7.40–7.25 (m, 5H), 5.67 (s, 1H), 3.96 (s, 2H), 3.63 (s, 2H), 2.99 (s, 2H), 2,54 (t, J=9.6 Hz, 2H), 2.22–2.12 (m, 2H).

(C) To a solution of this material (27 mmol) in 100 mL of methylene chloride is added triethylamine (51 mmol) in a single portion at 0° C. followed by acetic anhydride (51 mmol) dropwise via addition funnel at 0° C. The reaction mixture is allowed to warm to room temperature and stirred for an additional 2 hours. Solvents are removed in vacuo and the residue dried under vacuum.

(D) This material is dissolved in 200 mL of methylene chloride. Proton sponge (2.5 mmol) is added in a single portion and the reaction mixture cooled to 0° C. Benzyl chloroformate (53 mmol) is added dropwise via addition funnel and the reaction mixture allowed to warm to room temperature. Stirring is continued for 2 hours at room temperature. The reaction mixture is diluted with ethyl acetate (200 mL) and washed with 1N hydrochloric acid (3×100 mL), water and brine. The organic layer is worked up to provide N-Benzyloxycarbonyl-3-acetoxymethyl-1,2,5,6-tetrahydropyridine. $^1$H NMR (CDCl$_3$) δ7.40–7.25 (m, 5H), 5.90 (s, 1H), 5.14 (s, 2H), 4.47 (s, 2H), 3.95 (s, 2H), 3.54 (t, J=9.6Hz, 2H), 2.23–2.13 (m, 2H), 2.04 (s, 3H).

(E) To a solution of the acetate (20 mmol) in 75 mL of methanol is added sodium methoxide (20 mmol) portionwise at 0° C. Stirring is continued for 30 minutes at 0° C. The reaction mixture is diluted with 1N hydrochloric acid (10 mL) and methanol is removed in vacuo. The residue is taken up in ethyl acetate (200 mL) and washed with water (3×50 mL). The organic phase is worked up to provide the alcohol. To a solution of this alcohol in 100 mL of tetrahydrofuran is added triphenylphosphine (22 mmol) in a single portion at 0° C., followed by carbon tetrabromide (22 mmol) in a similar fashion. The reaction mixture is allowed to warm to room temperature and stirred at room temperature for 16 hours. Solvents are removed in vacuo and the residue is filtered through a column of silica gel using methylene chloride as eluent. The bromide thus obtained is dissolved in 200 mL of acetone along with sodium iodide (30 mmol) and the reaction mixture heated at reflux for 90 minutes. After cooling, acetone is removed in vacuo and the residue taken up into ethyl acetate (300 mL) and washed with water (2×100 mL). The organic layer is worked up and the N-Benzyloxycarbonyl-3-iodomethyl-1,2,5,6-tetrahydropyridine is used without further purification. $^1$H NMR (CDCl$_3$) δ7.40–7.25 (m, 5H), 6.04 (s, 1H), 5.13 (s, 2H), 4.12 (s, 2H), 3.86 (s, 2H), 3.53 (t, J=9.6 Hz, 2H), 2.13–1.98 (m, 2H).

Intermediate Example 4

N-tert-butoxycarbonylamino-2-(R)-((N-Benzyloxycarbonyl)-3-(1,2,5,6-tetrahydropyridylmethyl))-3-(R)-methyl β-alanine methyl ester

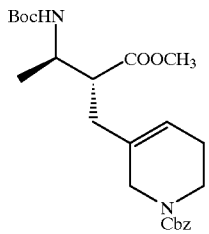

A solution of the compound of Intermediate Example 1 (11 mmol) in 70 mL of dry tetrahydrofuran is cooled to −78° C. and a solution of lithium hexamethyldisilazide in tetrahydrofuran (33 mmol) is added via syringe at such a rate that the temperature did not rise above −60° C. The reaction mixture is warmed to −25° C. over 40 minutes and recooled to −78° C. A solution of the compound of Intermediate Example 3 (27 mmol) in 20 mL of tetrahydrofuran is added via syringe at such a rate that the temperature did not rise above −60° C. The reaction mixture is allowed to come to room temperature and stirred at room temperature for 1 hour.

125 mL of saturated sodium bicarbonate is added and tetrahydrofuran is removed in vacuo. The remaining material is partitioned between 500 mL of ethyl acetate and 150 mL of saturated sodium bicarbonate. The organic phase is further washed with saturated sodium bicarbonate (2×100 mL) and brine. The organic layer is dried over magnesium sulfate, filtered, concentrated in vacuo. The residue is triturated with 40 mL of 4:1 hexanes:ethyl acetate. The solid material is filtered off and discarded. The filtrate, containing the desired product, is concentrated in vacuo.

Intermediate Example 5

N-tert-butoxycarbonylamino-2-(R)-((N-Benzyloxycarbonyl)-3-(1,2,5,6-tetrahydropyridylmethyl)) 3-(R)-ethyl β-alanine methyl ester

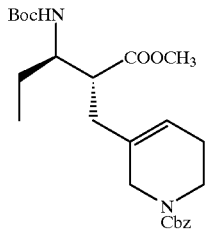

The compound of Intermediate Example 5 is prepared in the same fashion as the compound of Intermediate Example 4 substituting the compound of Intermediate Example 2 for the compound of Intermediate Example 1.

Intermediate Example 6

2-(R)-((N-Benzyloxycarbonyl)-3-(1,2,5,6-tetrahydropyridylmethyl))-3-(R)-methyl-β-alanine methyl ester

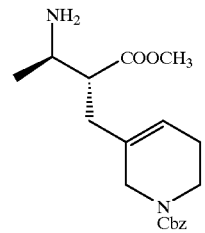

To a solution of the compound of Intermediate Example 4 (5 mmol) in 60 mL of methylene chloride is added 20 mL of trifluoroacetic acid, dropwise at 0° C. The resulting solution is stirred for 2 hours at 0° C. Solvents are removed in vacuo and the residue purified by reverse phase HPLC using a gradient of 30% to 70% acetonitrile in water containing 0.1% trifluoroacetic acid.

Acetonitrile is removed in vacuo and the remaining material partitioned between saturated sodium bicarbonate and ethyl acetate. The aqueous layer is extracted twice with ethyl acetate and the combined organic layers are dried over magnesium sulfate, filtered, and concentrated in vacuo.

Intermediate Example 7

2-(R)-((N-Benzyloxycarbonyl)-3-(1,2,5,6tetrahydropyridylmethyl))-3-(R)-ethyl β-alanine methyl ester

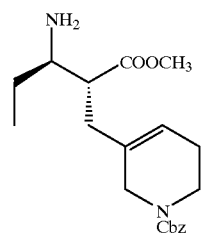

The compound of Intermediate Example 7 is prepared in the same fashion as the compound of Intermediate Example 6 substituting the compound of Intermediate Example 5 for the compound of Intermediate Example 4.

Intermediate Example 8

N-(4-phenyl)-benzoyl-2-(R)-((N-Benzyloxycarbonyl)-3-(1,2,5,6-tetrahydropyridylmethyl))-3-(R)-methyl β-alanine methyl ester

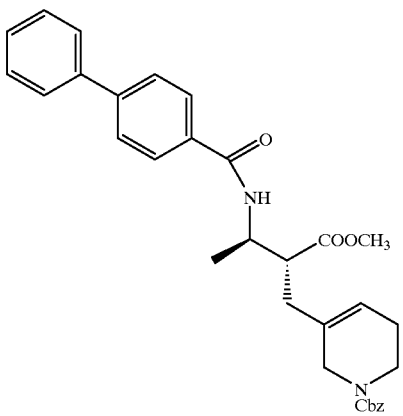

To a solution of 4-phenyl-benzoic acid (2 mmol) in 10 mL of DMF is added diisopropyl ethylamine (2 mmol) in a single portion at room temperature, followed by 2-(1H-benzotriazol-1-yl)-1,1,3,3-tetramethyluronium tetrafluoroborate (2 mmol) in a similar fashion. The reaction mixture is stirred for 2 minutes at room temperature and a solution of the compound of Intermediate Example 6 (2 mmol) in 15 mL of dimethylformamide is added in a single portion. Stirring is continued overnight at room temperature.

The reaction mixture is diluted with 300 mL of ethyl acetate and washed sequentially with 1N hydrochloric acid (3×75 mL), water, saturated sodium bicarbonate (3×75 mL) and brine. The organic phase is worked up.

Intermediate Example 9

4-((3-N-(tert-butoxycarbonyl)aminomethyl)-phenyl)-benzoic acid

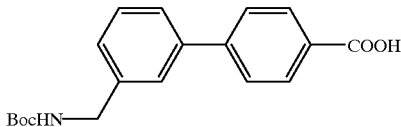

(A) To a solution of 11.8 mL of n-butyl lithium in hexanes (19 mmol) in 13 mL of tetrahydrofuran is added a solution of 1-bromo-3-cyano-benzene (19 mmol) in 2 mL of tetrahydrofuran, dropwise via syringe at −78° C. Stirring is continued for 1 hour at −78° C. A solution of zinc chloride (19 mmol) in 38 mL of tetrahydrofuran is added over 2 minutes at −78° C. The resulting solution is allowed to come to room temperature over 40 minutes.

(B) To a solution of bis(triphenylphosphine) palladium dichloride (1 mmol) in 11 mL of tetrahydrofuran is added diisobutyl aluminum hydride (1 mmol) as a solution in hexanes, at room temperature, followed by methyl iodobenzoate(16 mmol) in a single portion at room temperature.

Solution (A) is added to solution (B) and the reaction mixture allowed to stir at room temperature overnight. The reaction mixture is diluted with 300 mL of diethyl ether and washed with 1N hydrochloric acid (3×75 mL) and brine. The organic layer is worked up to provide methyl 4-(3-cyanophenyl)-benzoate.

Ammonia gas is bubbled into a suspension of the nitrile (24 mmol) in 200 mL of methanol for five minutes. To the resulting solution is added rhodium on alumina (5 g) and the suspension is shaken under a positive pressure of hydrogen for 36 hours. Catalyst is filtered off and methanol is removed in vacuo to give an oil which is triturated with ether and filtered.

A solution of the amine (15.4 mmol), triethylamine (17 mmol), di-tertbutyl dicarbonate (15.4 mmol), and 4-dimethylaminopyridine (1.5 mmol) in 60 mL of dimethylformamide is stirred at room temperature overnight. The solution is diluted with 800 mL of ethyl acetate and washed with 1N hydrochloric acid (3×150 mL) and brine. The organic layer is worked up and purified by flash chromatography (3:2 hexanes:ethyl acetate).

To a suspension of this material (1.6 mmol) in 10 mL of methanol and 20 mL of tetrahydrofuran is added 10 mL of 2N sodium hydroxide, dropwise at room temperature. The resulting solution is allowed to stir at room temperature for 2 hours. Organic solvents are removed in vacuo and the residue diluted with 20 mL of water and brought to pH 2 with 1N hydrochloric acid. Solid material is filtered off and dried under vacuum to give 4-((3-N-(tert-butoxycarbonyl-aminomethyl)-phenyl)-benzoic acid.

Intermediate Example 10

N-4-((3-N-(tert-butoxycarbonyl)-aminomethyl)-phenyl)-benzoyl-2-(R)-((N-Benzyloxycarbonyl)-3-(1,2,5,6-tetrahydropyridylmethyl))-3-(R)-methyl β-alanine methyl ester

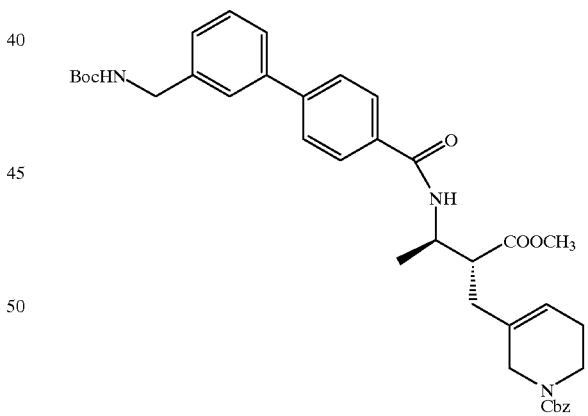

The compound of Intermediate Example 10 is prepared in an identical manner to the compound of Intermediate Example 8, substituting the compound of Intermediate Example 9 for 4-phenyl-benzoic acid.

Intermediate Example 11

4-(5-imidazolyl)-benzoyl-2-(R)-((N-Benzyloxycarbonyl)-3-(1,2,5,6-tetrahydropyridylmethyl))-3-(R)-methyl β-alanine methyl ester

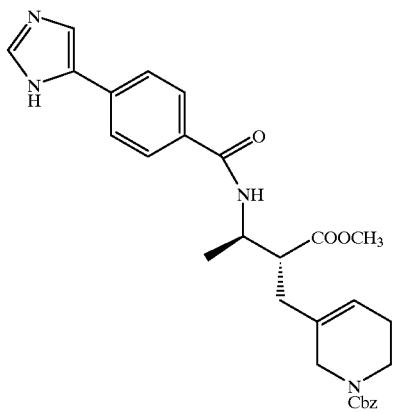

The compound of Intermediate Example 11 is prepared in an identical manner to the compound of Intermediate Example 8, substituting 4-(5-imidazolyl)-benzoic acid for 4-phenyl-benzoic acid.

Intermediate Example 12

N-4-((3-N-(tert-butoxycarbonyl)-aminomethyl)-phenyl)-benzoyl-2-(R)-((N-Benzyloxycarbonyl)-3-(1,2,5,6-tetrahydropyridylmethyl))-3-(R)-ethyl β-alanine methyl ester

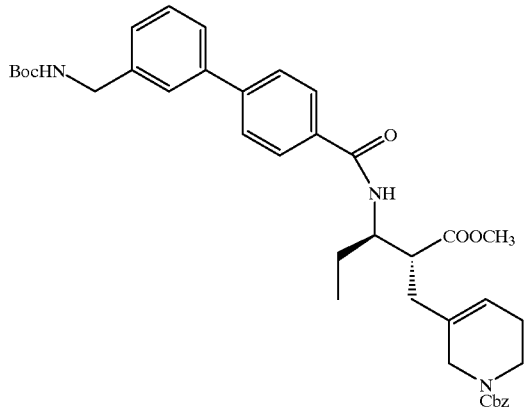

The compound of Intermediate Example 12 is prepared in an identical manner to the compound of Intermediate Example 10, substituting the compound of Intermediate Example 7 for the compound of Intermediate Example 6.

Intermediate Example 13

N-tert-butoxycarbonyl-3-iodomethyl-1,2,5,6-tetrahydropyridine

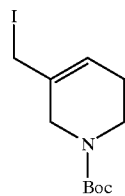

To a solution of the compound of Intermediate Example 3(C) in 200 mL of methylene chloride is added proton sponge (2.5 mmol) in a single portion at 0° C. 1-Chloroethyl chloroformate (53 mmol) is added dropwise via addition funnel and the reaction mixture allowed to warm to room temperature. Stirring is continued for 2 hours at room temperature. The reaction mixture is diluted with ethyl acetate (200 mL) and washed with 1N hydrochloric acid (3×100 mL), water and brine. The organic layer is worked up to provide N-2-chloroethoxycarbonyl-3-acetoxymethyl-1,2,5,6-tetrahydropyridine.

This material is dissolved in 150 mL of methanol and heated at reflux for one hour to provide, after removal of solvents in vacuo, 3-acetoxymethyl-1,2,5,6-tetrahydropyridine.

A solution of this material (15.4 mmol), triethylamine (17 mmol), di-tertbutyl dicarbonate (15.4 mmol), and 4-dimethylaminopyridine (1.5 mmol) in 60 mL of dimethylformamide is stirred at room temperature overnight. The solution is diluted with 800 mL of ethyl acetate and washed with 1N hydrochloric acid (3×150 mL) and brine. The organic layer is worked up and purified by flash chromatography (3:2 hexanes:ethyl acetate) to provide N-tert-butoxycarbonyl-3-acetoxymethyl-1,2,5,6-tetrahydropyridine.

This material is converted to N-tert-butoxycarbonyl-3-iodomethyl-1,2,5,6-tetrahydropyridine using the procedures described in Example 3(E).

Intermediate Example 14

N-(4-phenyl)-benzoyl-2-(R)-((N-tert-butoxycarbonyl)-3-(1,2,5,6-tetrahydropyridylmethyl))-3-(R)-methyl β-alanine methyl ester

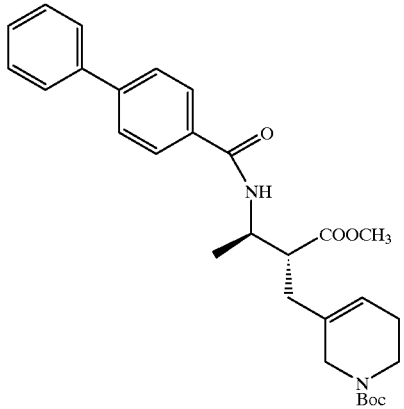

The compound of Intermediate Example 14 is prepared in a manner substantially similar to the compound of Intermediate Example 8, substituting the compound of Intermediate Example 13 for the compound of Intermediate Example 3 in the sequence.

Intermediate Example 15

N-4-((3-N-(tert-butoxycarbonyl)-aminomethyl)-phenyl)-benzoyl-2-(R)-3-(piperidinylmethyl)-3-(R)-methyl β-alanine methyl ester

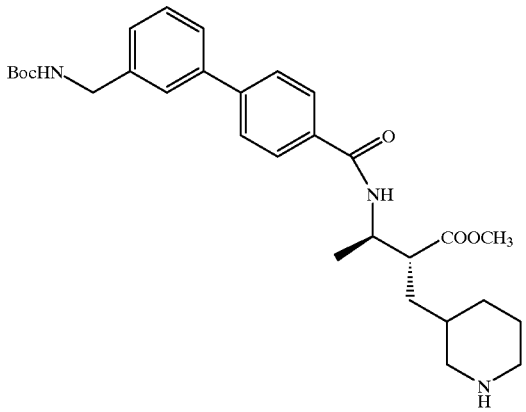

The compound of Intermediate Example 15 is prepared in a manner identical to the compound of Example 3, substituting the compound of Intermediate Example 10 for the compound of Intermediate Example 8.

Intermediate Example 16
N-4-((3-N-(tert-butoxycarbonyl)-aminomethyl)-phenyl)-benzoyl-2-(R)-3-(piperidinylethyl)-3-(R)-methyl β-alanine methyl ester

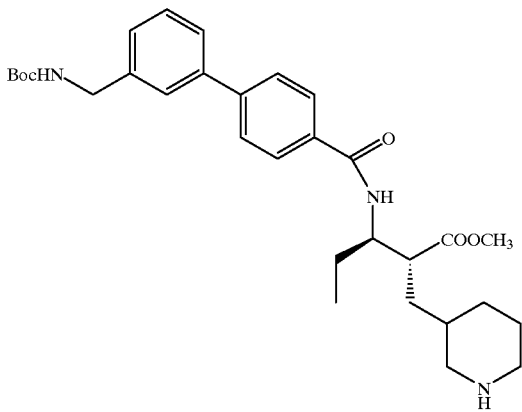

The compound of Intermediate Example 16 is prepared in a manner identical to the compound of Example 3, substituting the compound of Intermediate Example 12 for the compound of Intermediate Example 8.

Intermediate Example 17
N-Benzyloxycarbonyl-4-iodomethyl-1,2,5,6-tetrahydropyridine

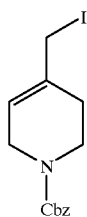

The compound of Intermediate Example 17 is prepared in a manner identical to the compound of Intermediate Example 3 starting from 4-pyridyl carbinol.

Intermediate Example 18
N-tert-butoxycarbonyl-4-iodomethyl-1,2,5,6-tetrahydropyridine

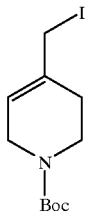

The compound of Intermediate Example 17 is prepared in a manner identical to the compound of intermediate Example 13 starting from 4-pyridyl carbinol.

Intermediate Example 19

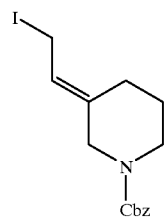

To a solution of 3-piperidone (12 mmol) in 200 mL of methylene chloride. is added triethylamine (18 mmol) in a single portion at room temperature and the reaction mixture cooled to 0° C. Benzyl chloroformate (12 mmol) is added dropwise via addition funnel and the reaction mixture allowed to warm to room temperature. Stirring is continued for 2 hours at room temperature. The reaction mixture is diluted with ethyl acetate (200 mL) and washed with 1N hydrochloric acid (3×100 mL), water and brine. The organic layer is worked up to provide N-Benzyloxycarbonyl-3-piperidone.

A solution of this material (12 mmol) and methyl triphenylphosphoranylidene acetate (12 mmol) in toluene is heated at reflux for 16 h. Toluene is removed in vacuo and the residue is subjected to flash chromatography (1:9 ethyl acetate:hexanes) to provide methyl (N-benzyloxycarbonyl)-3-piperidinylidene acetate.

To a solution of the methyl ester (3 mmol) in 30 mL of tetrahydrofuran is added diisobutylaluminum hydride (6 mmol) as a 1M solution in tetrahydrofuran, dropwise via syringe at −20° C. The reaction mixture is warmed to 0° C. and stirred for 2 h. The reaction mixture is cooled to −78° C. and excess diisobutylaluminum hydride is quenched by the dropwise addition of methanol. Solvents are removed in vacuo and the residue taken up in ethyl acetate (200 mL) and washed with a saturated solution of sodium tartrate (3×100 mL) and water (2×100 mL). The organic layer is worked up to give (N-benzyloxycarbonyl)-3-piperidinylidene ethanol.

To a solution of this alcohol in 100 mL of tetrahydrofuran is added triphenylphosphine (3 mmol) in a single portion at 0° C., followed by carbon tetrabromide (3 mmol) in a similar fashion. The reaction mixture is allowed to warm to room temperature and stirred at room temperature for 16 hours. Solvents are removed in vacuo and the residue is filtered through a column of silica gel using methylene chloride as eluent. The bromide thus obtained is dissolved in 200 mL of acetone along with sodium iodide (30 mmol) and the reaction mixture heated at reflux for 90 minutes. After cooling, acetone is removed in vacuo and the residue taken up into ethyl acetate (300 mL) and washed with water (2×100 mL). The organic layer is worked up and the 2-((N-benzyloxycarbonyl)3-piperidinylidene)-1-iodo-ethane is used without further purification.

EXAMPLE 1
N-(4-phenyl)-benzoyl-2-(R)-(3-(1,2,5,6-tetrahydropyridylmethyl))-3-(R)-methyl β-alanine methyl ester

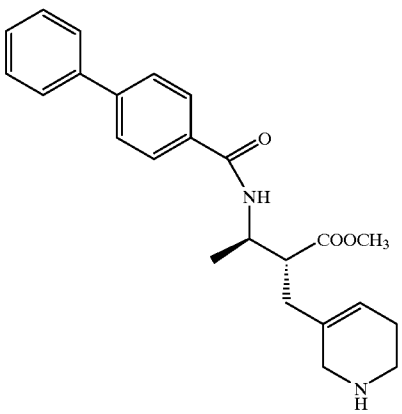

To a solution of the compound of Intermediate Example 14 (5 mmol) in 60 mL of methylene chloride is added 20 mL of trifluoroacetic acid, dropwise at 0° C. The resulting solution is stirred for 2 hours at 0° C. Solvents are removed in vacuo and the residue purified by reverse phase HPLC using a gradient of 10% to 60% acetonitrile in water containing 0.1% trifluoroacetic acid. $^1$H NMR (CD$_3$OD) δ7.9 (d, J=9.0 Hz, 2H), 7.7 (d, J=9.0 Hz, 2H), 7.6 (d, J=9.0 Hz, 2H), 7.4–7.6 (m, 3H), 5.7 (s, 1H), 4.5–4.6 (m, 1H), 3.6–3.7 (m, 1H), 3.7 (s, 3H), 3.5–3.6 (m, 2H), 3.2–3.3 (m, 2H), 2.8–2.9 (m, 1H), 2.3–2.6 (m, 4H), 1.30 (d, J=8.0 Hz, 3 Hz). MS (FAB) (M+H)$^+$ 394.

EXAMPLE 2
N-(4-phenyl)-benzoyl-2-(R)-(3-(N-aminoiminomethyl)-(1,2,5,6-tetrahydropyridylmethyl))-3-(R)-methyl, β-alanine methyl ester

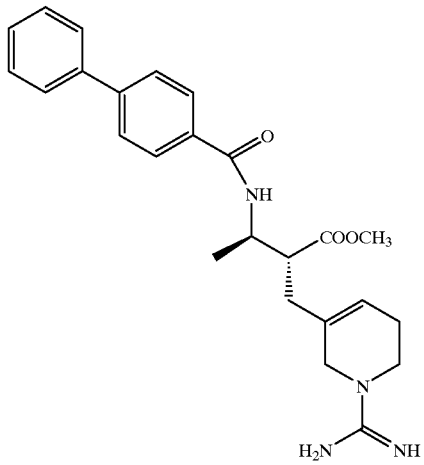

Part 1

To a solution of the compound of Example 1 (0.3 mmol) in 2 mL of methylene chloride is added triethylamine (1.2 mmol) in a single portion at 0° C. (N-Boc-amino-N-Boc-imino-methyl)-methyl thioether (0.33 mmol) is added portionwise at 0° C., followed by mercury (II) chloride (0.33 mmol) in a similar fashion. The reaction mixture is allowed to come to room temperature and stirred for 16 hours. The reaction mixture is filtered and the filtrate diluted with methylene chloride (25 mL) and washed with 5% hydrochloric acid (1×10 mL) and brine (1×25 mL). The organic phase is worked up.

Part 2

To a solution of this material in 6 mL of methylene chloride is added 2 mL of trifluoroacetic acid, dropwise at 0° C. The resulting solution is stirred for 2 hours at 0° C. Solvents are removed in vacuo and the residue purified by reverse phase HPLC using a gradient of 10% to 60% acetonitrile in water containing 0.1% trifluoroacetic acid. $^1$H NMR (CD$_3$OD) δ8.2 (d, J=10 Hz, 1H), 7.9 (d, J=9.0 Hz, 2H), 7.8 (d, J=9.0 Hz, 2H), 7.7 (d, J=9.0 Hz, 2H), 7.3–7.5 (m, 3H), 5.6 (s, 1H), 4.5–4.6 (m, 1H), 3.8–3.9 (m, 2H), 3.8 (s, 3H), 3.5–3.7 (m, 1H), 3.2–3.3 (m, 2H), 2.9–3.0 (m, 1H), 2.2–2.6 (m, 4H), 1.30 (d, J=8.0 Hz, 3 Hz). MS (FAB) (M+H)$^+$ 432.

EXAMPLE 3
N-(4-phenyl)-benzoyl-2-(R)-3-(piperidinylmethyl)-3-(R) methyl β-alanine methyl ester

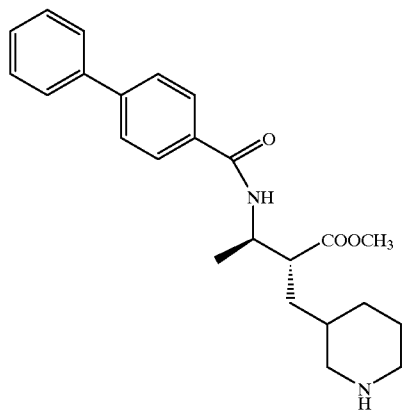

To a solution of the compound of Intermediate Example 8 (5 mmol) in 100 mL of methanol and 10 mL of acetic acid is added 10% palladium on charcoal (50 wt %). The reaction mixture is shaken under a positive pressure of hydrogen (45 psi) for 16 hours. The reaction mixture is filtered through celite and the filtrate concentrated in vacuo. The residue is taken up in ethyl acetate (200 mL) and washed with saturated sodium bicarbonate (3×100 mL). The organic layer is worked up to provide N-(4-phenyl)-benzoyl-2-(R)-3-(piperidinylmethyl)-3-(R)-methyl β-alanine methyl ester. $^1$H NMR (CD$_3$OD) (1:1 mixture of diastereomers) δ8.2 (d, J=9.0 Hz, 1H), 7.9 (d, J=9.0 Hz, 2H), 7.8 (d, J=9.0 Hz, 2H), 7.75 (d, J=8.0 Hz, 2H), 7.3–7.5 (m, 3H), 4.5–4.6 (m, 1H), 3.8–3.9 (m, 2H), 3.9 (s, 1.5H), 3.7 (s, 1.5H), 3.2–3.3 (m, 2H), 2.7–3.0 (m, 3H), 1.8–2.0 (m, 2H), 1.5–1.8 (m, 7H), 1.30 (d, J=8.0 Hz, 1.5 Hz), 1.0–1.2 (m, 1H). MS (FAB) (M+H)$^+$ 396.

EXAMPLE 4
4-(5-imidazolyl)-benzoyl-2-(R)-3-(piperidinylmethyl)-3-(R)-methyl β-alanine methyl ester

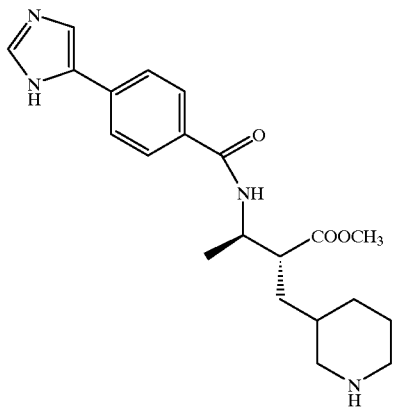

The compound of Example 4 is prepared in a manner identical to the compound of Example 3, substituting the compound of Intermediate Example 11 for the compound of Intermediate Example 8.

EXAMPLE 5

N-(4-phenyl)-benzoyl-2-(R)-3-(N-(aminoiminomethyl)-piperidinylmethyl)-3-(R)-methyl-β-alanine methyl ester

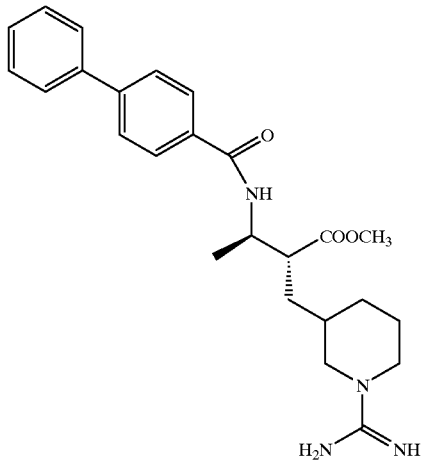

The compound of Example 5 is prepared in a manner identical to the compound of Example 2, substituting the compound of Example 3 for the compound of Example 1. $^1$H NMR (CD$_3$OD) (1:1 mixture of diastereomers) δ8.3 (d, J=10.0 Hz, 1H), 7.9 (d, J=9.0 Hz, 2H), 7.8 (d, J=9.0 Hz, 2H), 7.7 (d, J=9.0 Hz, 2H), 7.4–7.6 (m, 3H), 4.5–4.6 (m, 1H), 3.7–3.8 (m, 2H), 3.7 (s, 1.5H), 3.6 (s, 1.5H), 2.8–3.1 (m, 3H), 1.4–2.0 (m, 8H), 1.30 (d, J=8.0 Hz, 3 Hz). MS (FAB) (M+H)$^+$ 434.

EXAMPLE 6

N-4-((3-aminomethyl)-phenyl)-benzoyl-2-(R)-3-N-(aminoininomethyl)-piperidinyimethyl)-3-(R)-methyl β-alanine methyl ester

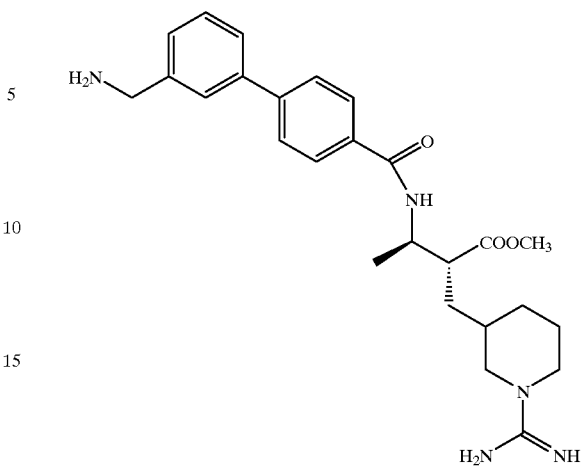

The compound of Example 6 is prepared in a manner identical to the compound of Example 2, substituting the compound of Intermediate Example 15 for the compound of Example 1. $^1$H NMR (CD$_3$OD) (1:1 mixture of diastereomers) δ8.3 (dd, J=4.0, 10.0 Hz, 1H), 7.95 (d, J=9.0 Hz, 2H), 7.8–7.9 (m, 4H), 7.4–7.6 (m, 2H), 4.4–4.6 (m, 1H), 4.2 (s, 2H), 3.7–3.8 (m, 1H), 3.7–3.8 (m, 2H), 3.7 (s, 1.5H), 3.6 (s, 1.5H), 3.2–3.0 (m, 1H), 2.8–3.1 (m, 2H), 1.4–2.0 (m, 8H), 1.30 (d, J=4.0 Hz, 1.5 Hz), 1.27 (d, J=6.0 Hz, 1.5 Hz). MS (FAB) (M+H)$^+$ 581.

EXAMPLE 7

4-(5-imidazolyl)-benzoyl-2-(R$^3$-N-(aminoiminimetyl)-piperidinylmethyl)-3-(R)-methyl-β-alanine methyl ester

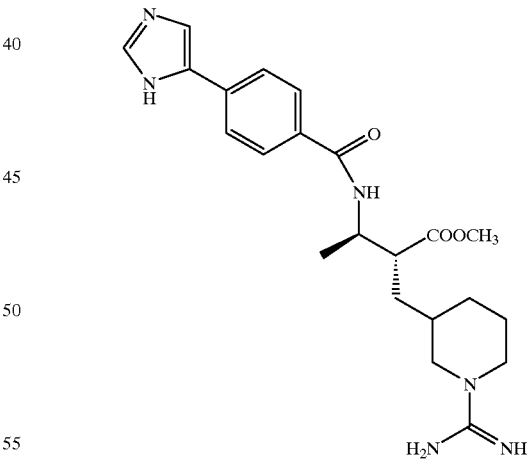

The compound of Example 7 is prepared in a manner identical to the compound of Example 2, substituting the compound of Example 4 for the compound of Example 1. $^1$H NMR (CD$_3$OD) (1:1 mixture of diastereomers) δ9.0 (s, 1H), 8.4 (dd, J=4.0, 10.0 Hz, 1H), 8.1 (s, 1H), 8.0 (d, J=9.0 Hz, 2H), 7.9 (d, J=9.0 Hz 2H), 4.5–4.6 (m, 1H), 3.8–3.9 (m, 2H), 3.9 (s, 1.5H), 3.7 (s, 1.5H), 3.1–3.2 (m, 1H), 2.8–3.0 (m, 2H), 1.4–2.0 (m, 8H), 1.30 (d, J=4.0 Hz, 1.5 Hz), 1.25 (d, J=6.0 Hz, 1.5 Hz), 1.1–1.3 (m, 1H). MS (FAB) (M+H)$^+$ 542.

EXAMPLE 8
N-4-((3-aminomethyl)-phenyl)-benzoyl-2-(R)-3-N-(aminoininomethyl)-piperidinylmethyl)-3-(R)-ethyl β-alanine methyl ester

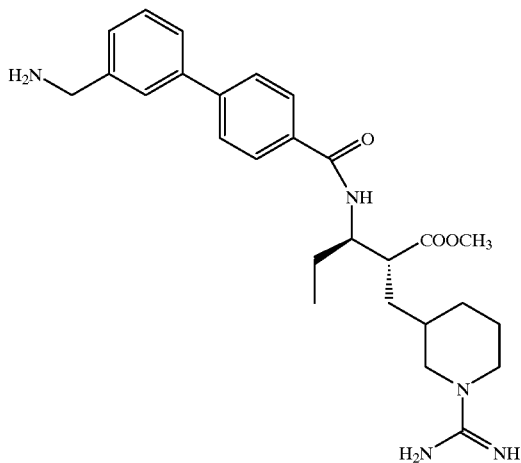

The compound of Example 8 is prepared in a manner identical to the compound of Example 2, substituting the compound of Intermediate Example 16 for the compound of Example 1. $^1$H NMR (CD$_3$OD) (1:1 mixture of diastereomers) δ7.95–7.86 (m, 2H), 7.83–7.70 (m, 4H), 7.60–7.45 (m, 2H), 4.32–4.22 (m, 1H), 4.21 (s, 2H), 3.82–3.72 (m, 2H), 3.71 (s, 3H), 3.10–2.95 (m, 1H), 2.70–3.1 (m, 3H), 2.07–1.83 (m, 1H), 1.82–1.38 (m, 7H), 1.35–1.12 (m, 1H), 0.98 (t, J=8.4 Hz, 3 Hz).

EXAMPLE 9
N-(4-phenyl)-benzoyl-2-(R)-(4-(1,2,5,6-tetrahydropyridylmethyl))-3-(R)-methyl β-alanine methyl ester

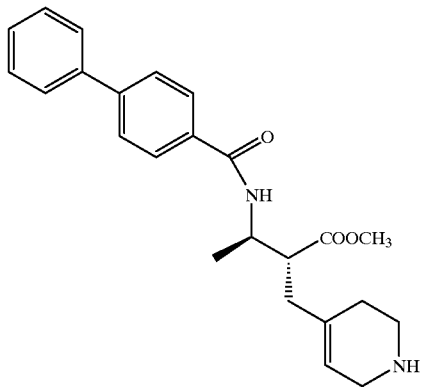

The compound of Example 9 is prepared in the same fashion as the compound of Example 1, substituting the compound of Intermediate Example 18 for the compound of Intermediate Example 13 in the sequence. $^1$H NMR (CD$_3$OD) δ7.9 (d, J=9.0 Hz, 2H), 7.8 (d, J=9.0 Hz, 2H), 7.7 (d, J=9.0 Hz, 2H), 7.4–7.6 (m, 3H), 5.8 (s, 1H), 4.5–4.6 (m, 1H), 3.6–3.9 (m, 3H), 3.8 (s, 3H), 3.2–3.4 (m, 2H), 2.8–2.9 (m, 1H), 2.3–2.5 (m, 4H), 1.30 (d, J=8.0 Hz, 3 Hz). MS (FAB) (M+H)$^+$ 394.

EXAMPLE 10
N-(4-phenyl)benzoyl-2-(R)-(4-(N-aminoiminomethyl)-(1,2,5,6-tetrahydroynridylmethyl))-3-(R)-methyl β-alanine methyl ester

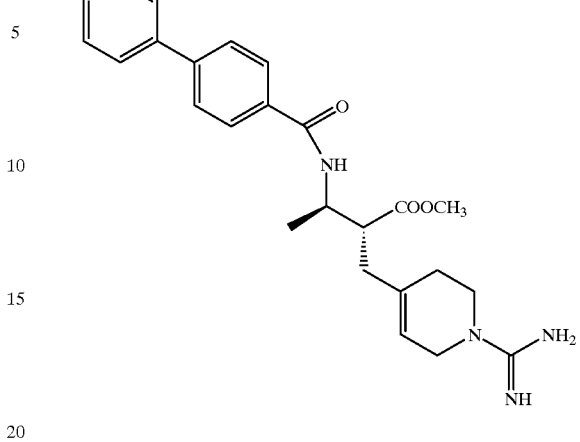

The compound of Example 10 is prepared in the same fashion as the compound of Example 2, substituting the compound of Intermediate Example 18 for the compound of Intermediate Example 13 in the sequence. $^1$H NMR (CD$_3$OD) δ8.3 (d, J=10.0 Hz, 1H), 7.9 (d, J=9.0 Hz, 2H), 7.8 (d, J=9.0 Hz, 2H), 7.7 (d, J=9.0 Hz, 2H), 7.4–7.5 (m, 3H), 5.8 (s, 1H), 4.4–4.5 (m, 1H), 3.8–4.0 (m, 2H), 3.7 (s, 3H), 3.4–3.5 (m, 2H), 3.2–3.3 (m, 1H), 2.9–3.1 (m, 1H), 2.4–2.5 (m, 2H), 2.2–2.3 (m, 2H), 1.30 (d, J=8.0 Hz, 3 Hz). MS (FAB) (M+H)$^+$ 436.

EXAMPLE 11
N-(4-phenyl)-benzoyl-2-(R)-4-(piperidinylmethyl)-3-(R)-methyl β-alanine methyl ester

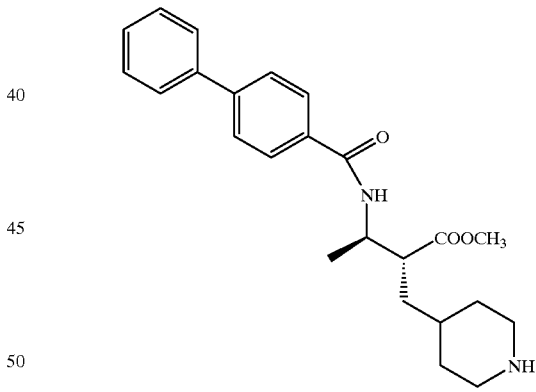

The compound of Example 11 is prepared using procedures substantially similar to those used to prepare the compound of Example 3, substituting the compound of Intermediate Example 18 for the compound of Intermediate Example 3 in the sequence. $^1$H NMR (CD$_3$OD) (1:1 mixture of diastereomers) δ8.3 (d, J=10.0 Hz, 1H), 7.9 (d, J=9.0 Hz, 2H), 7.7 (d, J=9.0 Hz, 2H), 7.6 (d, J=9.0 Hz, 2H), 7.4–7.5 (m, 3H), 4.4–4.5 (m, 1H), 3.7–3.8 (m, 1H), 3.7 (s, 3H), 2.8–3.0 (m, 4H), 1.3–2.1 (m, 8H), 1.30 (d, J=8.0 Hz, 3 Hz). MS (FAB) (M+H)$^+$ 396.

EXAMPLE 12
N-(4-phenyl)-benzoyl-2-(R)-4-(N-(aminoiminomethyl)-piperidiniylmethyl)-3-(R)-methyl-β-alanine methyl ester

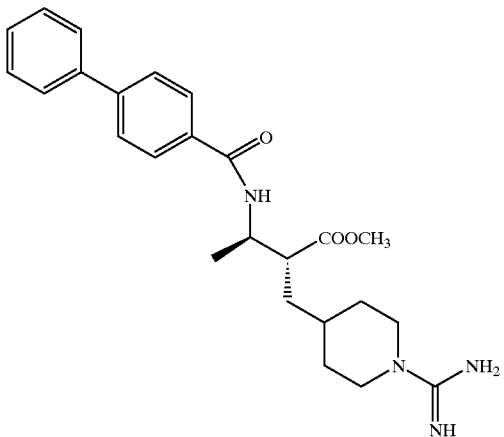

The compound of Example 12 is prepared using procedures substantially similar to those used to prepare the compound of Example 5, substituting the compound of Intermediate Example 18 for the compound of Intermediate Example 3 in the sequence. $^1$H NMR (CD$_3$OD) (1:1 mixture of diastereomers) δ8.3 (d, J=10.0 Hz, 1H), 7.9 (d, J=9.0 Hz, 2H), 7.7 (d, J=9.0 Hz, 2H), 7.6 (d, J=9.0 Hz, 2H), 7.3–7.5 (m, 3H), 4.4–4.5 (m, 1H), 3.7–3.8 (m, 2H), 3.8 (s, 3H), 2.8–3.1 (m, 3H), 1.4–2.1 (m, 7H), 1.2–1.3 (m, 1H), 1.30 (d, J=8.0 Hz, 3 Hz). MS (FAB) (M+H)$^+$ 438.

EXAMPLE 13

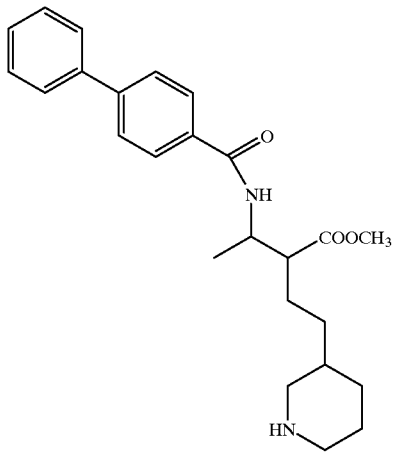

The compound of Example 13 is prepared in a manner identical to the compound of Example 3, substituting the compound of Intermediate Example 19 in the synthetic sequence.

EXAMPLE 14

3-(R)-[(3-Aminomethylbiphenyl-4-carbonyl)amino]-2-[1-(N-hydroxycarbamimidoyl)-piperidin-3-ylmethyl]butyric acid methyl ester ditrifluroacetate

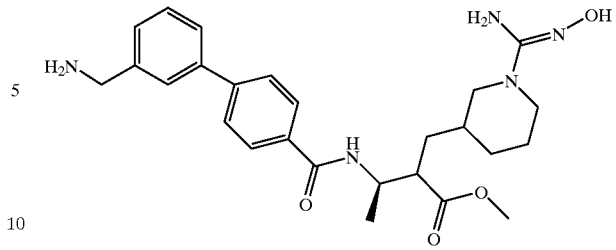

The compound of intermediate example 15 (2.5 mmol) is treated with methanol (20 mL), sodium acetate (12.5 mmol) and cyanogen bromide (5 mmol). After 1 h at room temperature the reaction is treated with water and ethyl acetate. The organic layer is separated, washed with water, dried over sodium sulfate and concentrated. The residue (~1.82 mmol) is treated with a solution of hydroxylamine i.e. the filtrate from the reaction of hydroxylamine hydrochloride (1.82 mmol), sodium carbonate (0.91 mmol) and methanol for 0.5 h. After 3 h the reaction is diluted with saturated bicarbonate and ethyl acetate. The organic layer is washed with water, dried over sodium sulfate and evaporated in vacuo to give 1 g of residue. This material was treated with trifluroacetic acid (15 mL) and methylene chloride (45 mL) at 0° C. for 3 h. The volatiles are removed in vacuo and the residue is subjected to HPLC, then lyophilized to give the title compound. $^1$H NMR (CD$_3$OD) (1:1 mixture of diastereomers); MS (M+H=482), δ, 8.35, 8.2 (two d, 1H), 7.9–8.0 (m, 2H), 7.7–7.8 (m, 2H), 7.55 (t, 1H), 7.45 (d, 1H), 4.35–4.5 (m 1H), 4.2 (s, 2H), 3.7–3.9 (m, 5H), 3.0–3.1 (m, 1H), 2.7–3.0 (m, 2H), 1.9–2.1 (m, 1H), 1.4–1.8 (m, 8H), 1.2–1.3 (m, 4H).

EXAMPLE 15

3-(R)-[(3-Aminomethylbiphenyl-4-carbonyl)amino]-2-[1-(N-ethoxcarbonylamino-imino-methyl)-piperidin-3-ylmethyl]-butyric acid methyl ester ditrifluroacetate

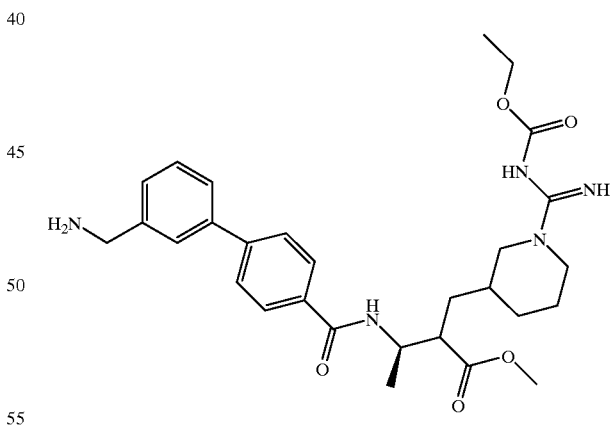

The compound of intermediate example 15 is treated as described in Example 2, Part 1 to give 0.18 mmol of N-4-((3-tert-butoxycarbonylaminomethyl)-phenyl)-benzoyl-2-(R)-3-N-(aminoininomethyl)-piperidinylmethyl)-3-(R)-methyl β-alanine methyl ester. This material is treated with N-methylpiperidine (87 μL, 0.18 mM) and ethyl chloroformate (18 μL, 0.72 mM) in DMF (1 mL) and methylene chloride (9 mL). The solution is stirred overnight at room temperature. Fresh N-methylpiperidine (20 μL) and ethyl chloroformate (18 μL) is added and the reaction stirred an additional 2 h. The solution is diluted with ethyl acetate, washed with water, 10% bicarbonate, dried over sodium sulfate to give about 110 mg (0.17 mM) of residue. The products of several runs are combined (0.83 mmol) and treated with trifluroacetic acid and methylene chloride as described in Example 14. The residue obtained is purified by HPLC to yield the title compound (0.64 mmol). $^1$H NMR (CD$_3$OD) (1:1 mixture of diastereomers) δ8.5, 8.4 (two d, 1H), 8.0–8.1 (m, 2H), 7.8–7.9 (m, 2H), 7.7 (t, 1H), 7.55 (d, 1H), 4.5–4.6 (m, 1H), 4.4 (q, 2H), 4.3, (s, 2H), 3.9–4.1 (m, 2H), 3.8 (d, 3H), 3.2–3.3 (m, 1H), 2.9–3.1 (m, 2H), 1.9–2.1 (m, 1H), 1.6–1.9 (m, 8H), 1.3–1.5 (m, 7H); MS (M+H=538).

In a like manner by the methods described above the following compounds are prepared:

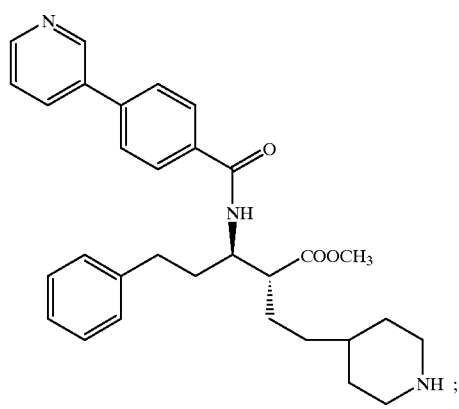

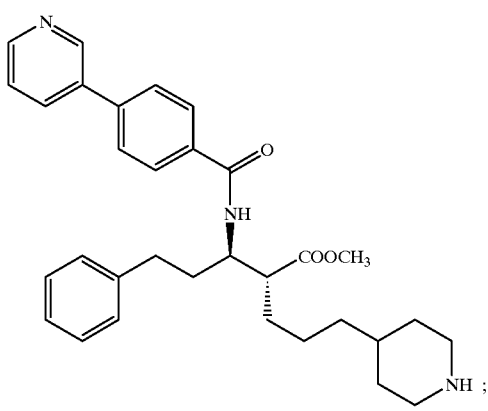

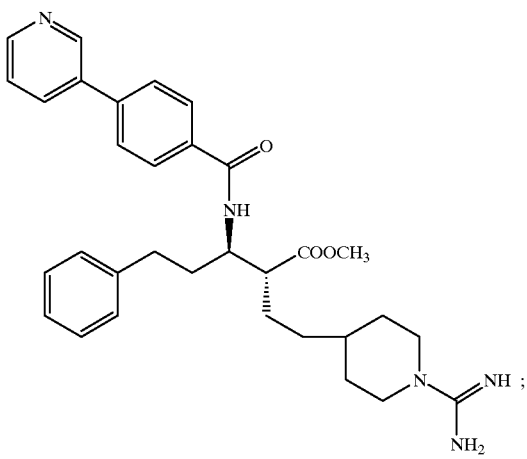

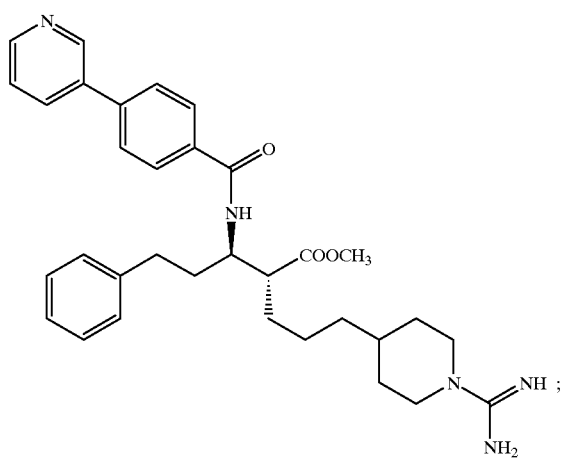

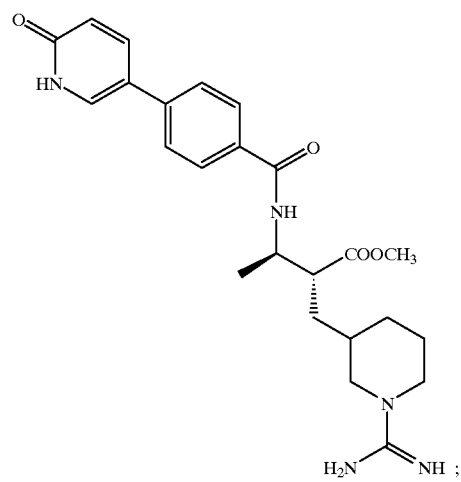

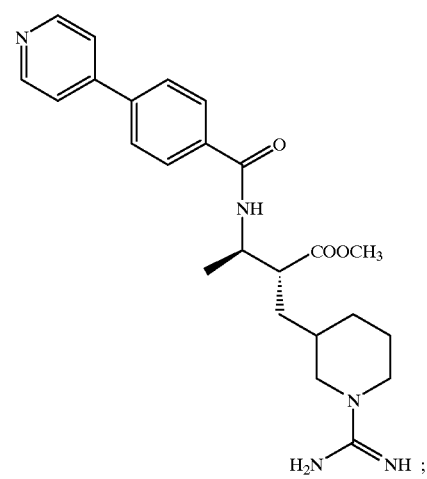

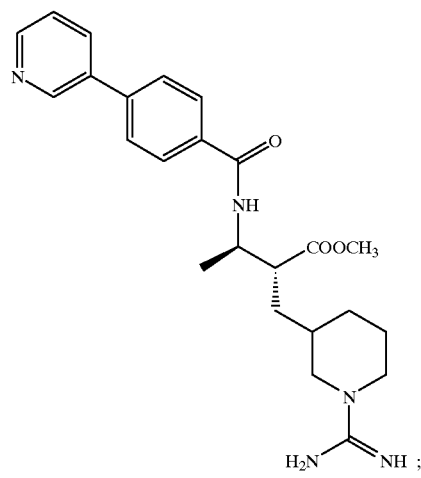
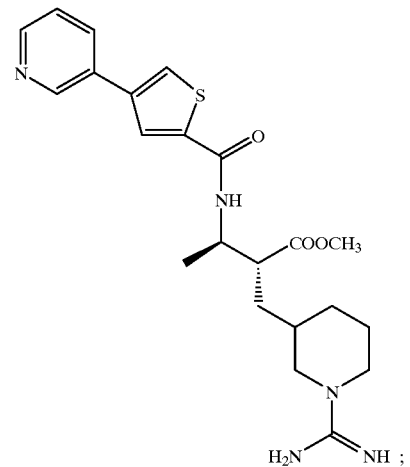
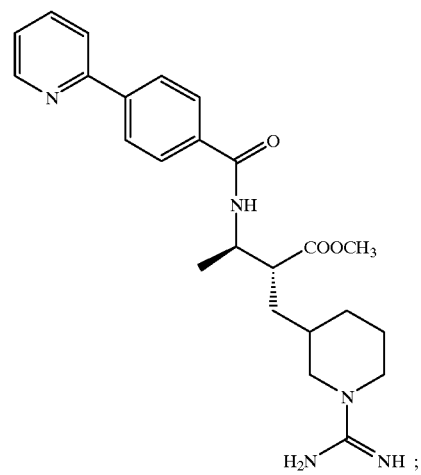
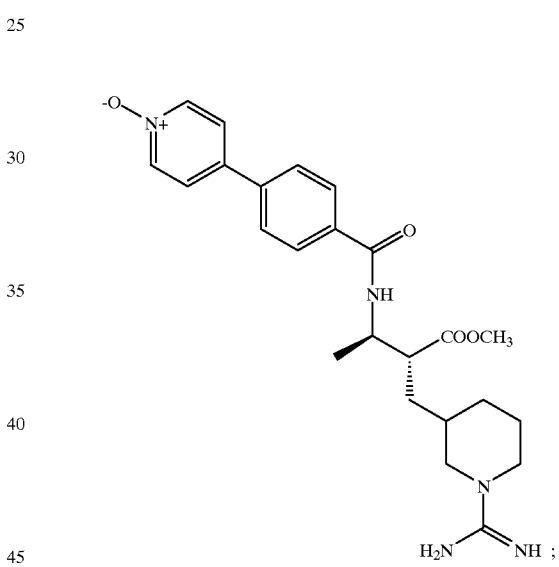
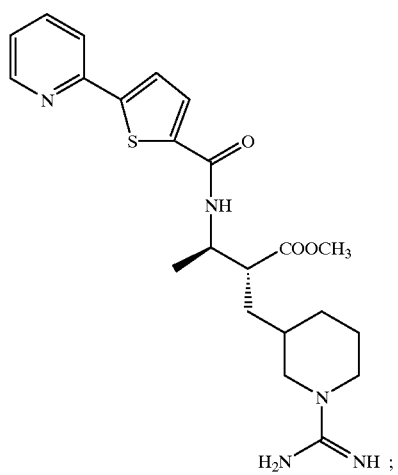
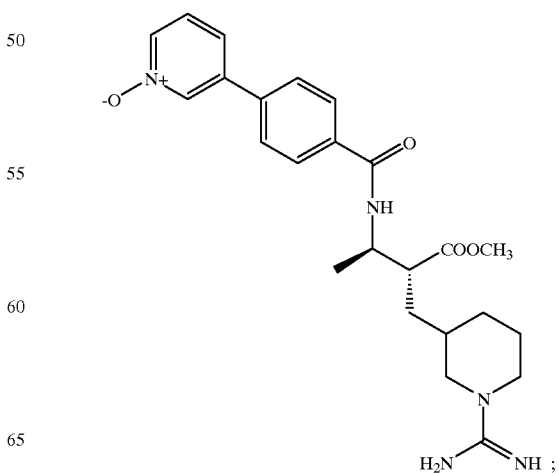

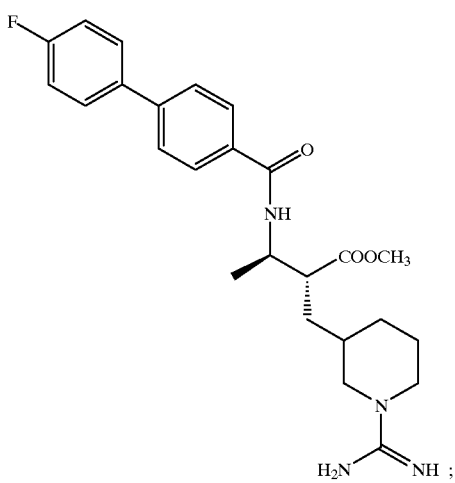

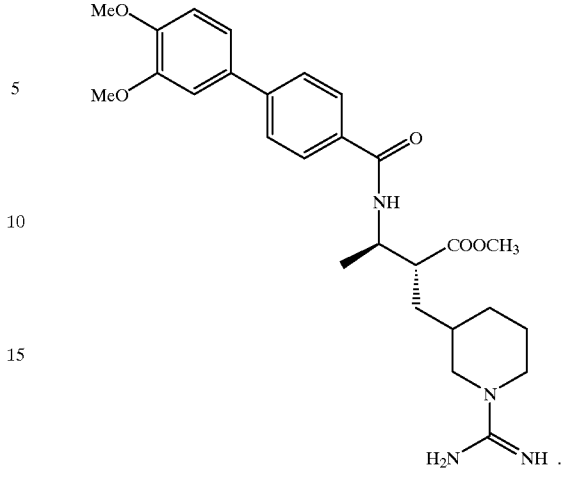

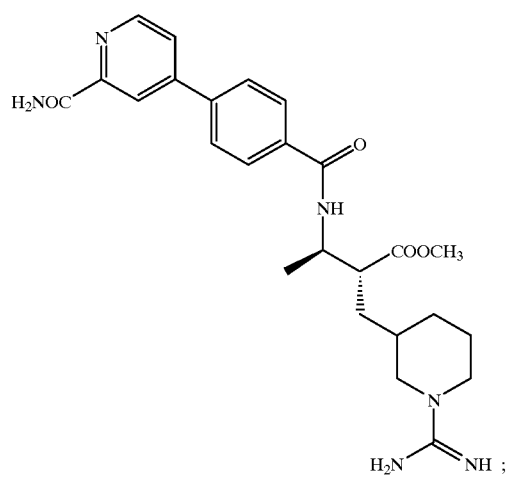

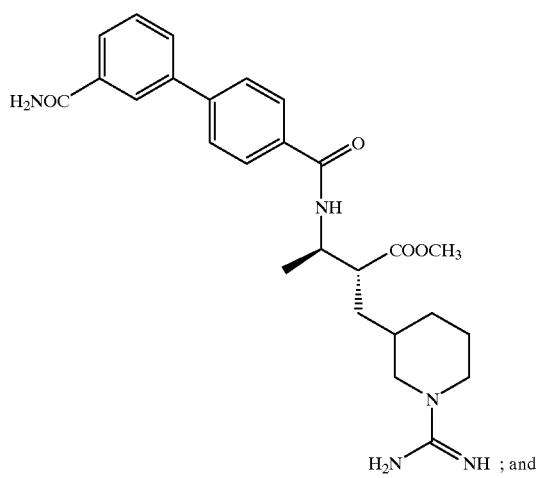

The molecules described herein inhibit blood coagulation by virtue of their ability to inhibit the activity of Factor Xa. Both free Factor Xa and Factor Xa assembled in the prothrombinase complex (Factor Xa, Factor Va, calcium and phospholipid) are inhibited. Factor Xa inhibition is obtained by direct complex formation between the inhibitor and the enzyme and is therefore independent of the plasma co-factor antithrombin III. Effective Factor Xa inhibition is achieved by administering the compounds either by oral administration, continuous intravenous infusion, bolus intravenous administration or any other parenteral route such that it achieves the desired effect of preventing the Factor Xa induced formation of thrombin from prothrombin.

Anticoagulant therapy is indicated for the treatment and prophylaxis of a variety of thrombotic conditions of both the venous and arterial vasculature. In the arterial system, abnormal thrombus formation is primarily associated with arteries of the coronary, cerebral and peripheral vasculature. The diseases associated with thrombotic occlusion of these vessels principally include acute myocardial infarction (AMI), unstable angina, thromboembolism, acute vessel closure associated with thrombolytic therapy and percutaneous transluminal coronary angioplasty (PTCA), transient ischemic attacks, stroke, intermittent claudication and bypass grafting of the coronary (CABG) or peripheral arteries. Chronic anticoagulant therapy may also be beneficial in preventing the vessel luminal narrowing (restenosis) that often occurs following PTCA and CABG, and in the maintenance of vascular access patency in long-tenn hemodialysis patients. With respect to the venous vasculature, pathologic thrombus formation frequently occurs in the veins of the lower extremities following abdominal, knee and hip surgery (deep vein thrombosis, DVT). DVT further predisposes the patient to a higher risk of pulmonary thromboembolism. A systemic, disseminated intravascular coagulopathy (DIC) commonly occurs in both vascular systems during septic shock, certain viral infections and cancer. This condition is characterized by a rapid consumption of coagulation factors and their plasma inhibitors resulting in the formation of life-threatening thrombin throughout the microvasculature of several organ systems. The indications discussed above include some, but not all, of the possible clinical situations where anticoagulant therapy is warranted. Those experienced ill this field are well aware of the circumstances requiring either acute or chronic prophylactic anticoagulant therapy.

These compounds may be used alone or in combination with other diagnostic, anticoagulant, antiplatelet or fibrinolytic agents. For example adjunctive administration of Factor Xa inhibitors with standard heparin, low molecular weight heparin, direct thrombin inhibitors (i.e. hirudin), aspirin, fibrinogen receptor antagonists. streptokinase, urokinase and/or tissue plasminogen activator may result in greater antithrombotic or thrombolytic efficacy or efficiency. The compounds described herein may be administered to treat thrombotic complications in a variety of animals such as primates including humans, sheep, horses, cattle, pigs, dogs, rats and mice. Inhibition of Factor Xa is useful not only in the anticoagulant therapy of individuals having thrombotic conditions but is useful whenever inhibition of blood coagulation is required such as to prevent coagulation of stored whole blood and to prevent coagulation in other biological samples for testing or storage. Thus, any Factor Xa inhibitor can be added to or contacted with any medium containing or suspected of containing Factor Xa and in which it is desired that blood coagulation be inhibited.

In addition to their use in anticoagulant therapy, Factor Xa inhibitors may find utility in the treatment or prevention of other diseases in which the generation of thrombin has been implicated as playing a pathologic role. For example, thrombin has been proposed to contribute to the morbidity and mortality of such chronic and degenerative diseases as arthritis, cancer, atherosclerosis and Alzheimer's disease by virtue of its ability to regulate many different cell types through specific cleavage and activation of a cell surface thrombin receptor. Inhibition of Factor Xa will effectively block thrombin generation and therefore neutralize any pathologic effects of thrombin on various cell types.

According to a further feature of the invention there is provided a method for the treatment of a human or animal patient suffering from, or subject to, conditions which can be ameliorated by the administration of an inhibitor of Factor Xa, for example conditions as hereinbefore described, which comprises the administration to the patient of a pharmaceutically effective amount of compound of formula I or a composition containing a compound of formula I.

The present invention also includes within its scope pharmaceutical formulations which comprise at least one of the compounds of Formula I in association with a pharmaceutically acceptable carrier or coating.

In practice compounds of the present invention may generally be administered parenterally, intravenously, subcutaneously intramuscularly, colonically, nasally, intraperitoneally, rectally or orally.

The products according to the invention may be presented in forms permitting administration by the most suitable route and the invention also relates to pharmaceutical compositions containing at least one product according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation or microfiltration.

Suitable compositions containing the compounds of the invention may be prepared by conventional means. For example, compounds of the invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of formula I.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.01 to about 100, preferably about 0.01 to about 10, mg/kg body weight per day by inhalation, from about 0.01 to about 100, preferably 0.1 to 70, more especially 0.5 to 10, mg/kg body weight per day by oral administration, and from about 0.01 to about 50, preferably 0.01 to 10, mg/kg body weight per day by intravenous administration. In each particular case, the doses will be determined in accordance with the factors distinctive to the subject to be treated, such as age, weight, general state of health and other characteristics which can influence the efficacy of the medicinal product.

The products according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

The compounds of the present invention may also be formulated for use in conjunction with other therapeutic agents such as agents or in connection with the application of therapeutic techniques to address pharmacological conditions which may be ameliorated through the application of a compound of formula I, as described herein.

The compounds of the present invention may be used in combination with any anticoagulant, antiplatelet, antithrombotic or profibrinolytic agent. Often patients are concurrently treated prior, during and after interventional procedures with agents of these classes either in order to safely perform the interventional procedure or to prevent deleterious effects of thrombus formation. Some examples of classes of agents known to be anticoagulant, antiplatelet, antithrombotic or profibrinolytic agents include any formulation of heparin, low molecular weight heparins, pentasaccharides, fibrinogen receptor antagonists, thrombin inhibitors, Factor Xa inhibitors, or Factor VIIa inhibitors.

The compounds of the present invention may be used in combination with any antihypertensive agent or cholesterol or lipid regulating agent, or concurrently in the treatment of restenosis, atherosclerosis or high blood pressure. Some examples of agents that are useful in combination with a compound according to the invention in the treatment of high blood pressure include compounds of the following classes; beta-blockers, ACE inhibitors, calcium channel antagonists and alpha-receptor antagonists. Some examples of agents that are useful in combination with a compound according to the invention in the treatment of elevated cholesterol levels or disregulated lipid levels include compounds known to be HMGCoA reductase inhibitors, compounds of the fibrate class, It is understood that the present invention includes combinations of compounds of the present invention with one or more of the aforementioned therapeutic class agents Compounds within the scope of the present invention exhibit marked pharmacological activities according to tests described in the literature and below which tests results are believed to correlate to pharmacological activity in humans and other mammals.

Enzyme Assays

The ability of the compounds in the present invention to act as inhibitors of Factor Xa, thrombin, trypsin, tissue-plasminogen activator (t-PA), urokinase-plasminogen activator (u-PA), plasmin and activated protein C is evaluated by determining the concentration of inhibitor which resulted in a 50% loss in enzyme activity (IC50) using purified enzymes.

All enzyme assays are carried out at room temperature in 96-well microtiter plates using a final enzyme concentration of 1 nM. The concentrations of Factor Xa and thrombin are determined by active site titration and the concentrations of all other enzymes are based on the protein concentration supplied by the manufacturer. Compounds according to the invention are dissolved in DMSO, diluted with their respective buffers and assayed at a maximal final DMSO concentration of 1.25%. Compound dilutions are added to wells containing buffer and enzyme and pre-equilibrated for between 5 and 30 minutes. The enzyme reactions are initiated by the addition of substrate and the color developed from the hydrolysis of the peptide-p-nitroanilide substrates is monitored continuously for 5 minutes at 405 nm on a Vmax microplate reader (Molecular Devices). Under these conditions, less than 10% of the substrate is utilized in all assays. The initial velocities measured are used to calculate the amount of inhibitor which resulted in a 50% reduction of the control velocity (IC50). The apparent Ki values are then determined according to the Cheng-Prusoff equation (IC50= Ki[1+[S]/Km]) assuming competitive inhibition kinetics.

An additional in vitro assay may be used to evaluate the potency of compounds according to the invention in normal human plasma. The activated partial thromboplastin time is a plasma-based clotting assay that relies on the in situ generation of Factor Xa, its assembly into the prothrombinase complex and the subsequent generation of thrombin and fibrin which ultimately yields the formation of a clot as the assay endpoint. This assay is currently used clinically to monitor the ex vivo effects of the commonly used anticoagulant drug heparin as well as direct acting antithrombin agents undergoing clinical evaluation. Therefore, activity in this in vitro assay is considered as a surrogate marker for in vivo anticoagulant activity.

Human Plasma Based Clotting Assay

Activated partial thromboplastin clotting times are determined in duplicate on a MLA Electra 800 instrument. A volume of 100 µl of citrated normal human pooled plasma (George King Biomedical) is added to a cuvette containing 100 µl of a compound according to the invention in Tris/NaCl buffer (pH 7.5) and placed in the instrument. Following a 3 minute warming period the instrument automatically adds 100 µl of activated cephaloplastin reagent (Actin, Dade) followed by 100 µl of 0.035 M $CaCl_2$ to initiate the clotting reaction. Clot formation is determined spectrophotometrically and measured in seconds. Compound potency is quantitated as the concentration required to double a control clotting time measured with human plasma in the absence of the compound according to the invention.

Compounds according to the invention may also be evaluated for their in vivo antithrombotic efficacy in two well established animal experimental models of acute vascular thrombosis. A rabbit model of jugular vein thrombosis and a rat model of carotid artery thrombosis are used to demonstrate the antithrombotic activity of these compounds in distinct animal model paradigms of human venous thrombosis and arterial thrombosis, respectively.

Experimental In Vivo Rabbit Venous Thrombosis Model

This is a well characterized model of fibrin rich venous thrombosis that is validated in the literature and shown to be sensitive to several anticoagulant drugs including heparin (Antithrombotic Effect of Recombinant Truncated Tissue Factor Pathway Inhibitor (TFPI 1-161) in Experimental Venous Thrombosis—a Comparison with Low Molecular Weight Heparin, J. Hoist, B. Lindblad, D. Bergqvist, O. Nordfang, P. B. Ostergaard, J. G. L. Petersen, G. Nielsen and U. Hedner. Thrombosis and Haemostasis, 71, 214–219 (1994). The purpose of utilizing this model is to evaluate the ability of compounds to prevent the formation of venous thrombi (clots) in vivo generated at a site of injury and partial stasis in the jugular vein.

Male and female New Zealand white rabbits weighing 1.5–2 kg are anesthetized with 35 mg/kg of ketamine and 5 mg/kg xylazine in a volume of 1 mL/kg (i.m.). The right jugular vein is cannulated for infusion of anesthetic (ketamine/xylazine 17/2.5 mg/kg/hr at a rate of approximately 0.5 mL/hr) and administration of test substances. The right carotid artery is cannulated for recording arterial blood pressure and collecting blood samples. Body temperature is maintained at 39° C. with a GAYMAR T-PUMP. The left external jugular vein is isolated and all side branches along an exposed 2–3 cm of vessel are tied off. The internal jugular vein is cannulated, just above the bifurcation of the common jugular, and the tip of the cannula is advanced just proximal to the common jugular vein. A 1 cm segment of the vein is isolated with non-traumatic vascular clamps and a relative stenosis is formed by tying a ligature around the vein with an 18G needle just below the distal most clamp. This creates a region of reduced flow and partial stasis at the injury site. The isolated segment is gently rinsed with saline 2–3 times via the cannula in the internal jugular. Thereafter the isolated segment is filled with 0.5 mL of 0.5% polyoxyethylene ether (W-1) for 5 minutes. W-1 is a detergent which disrupts the endothelial cell lining of the segment, thus providing a thrombogenic surface for initiating clot formation. After 5 minutes the W-1 is withdrawn from the segment, and the segment is again gently rinsed with saline 2–3 times. The vascular clamps are then removed, restoring blood flow through this portion of the vessel. Clot formation is allowed to form and grow for 30 minutes after which the vein is cut just below the stenotic ligature and inspected for blood flow (the absence of blood flow is recorded as complete occlusion). The entire isolated segment of vein is then ligated and the formed clot is removed and weighed (wet weight). The effect of test agents on final clot weights is used as the primary end point. Animals are maintained for an additional thirty minutes to obtain a final pharnacodynamic measure of anticoagulation. Drug administration is initiated 15 minutes prior to vascular injury with W-1 and continued through the period of clot formation and maturation. Three blood samples (3 mL each) are obtained for evaluation of hemostatic parameters: one just prior to administration of W-1; a second 30 minutes after removal of the vascular clamps and a third at the termination of the experiment. Antithrombotic efficacy is expressed as a reduction in the final clot weight in preparations treated with a compound according to the invention relative to vehicle treated control animals.

Experimental In Vivo Rat Arterial Thrombosis Model

The antithrombotic efficacy of Factor Xa inhibitors against platelet-rich arterial thrombosis may be evaluated using a well characterized rat carotid artery $FeCl_2$-induced thrombosis model (Superior Activity of a Thromboxane Receptor Antagonist as Compared with Aspirin in Rat Models of Arterial and Venous Thrombosis, W. A. Schumacher, C. L. Heran, T. E. Steinbacher, S. Youssef and M. L. Ogletree. Journal of Cardiovascular Pharmacology, 22, 526–533 (1993); Rat Model of Arterial Thrombosis Induced by Ferric Chloride, K. D. Kurtz, B. W. Main, and G. E. Sandusky. Thrombosis Research, 60, 269–280 (1990); The Effect of Thrombin Inhibition in a Rat Arterial Thrombosis Model, R. J. Broersma, L. W. Kutcher and E. F. Heminger. Thrombosis Research 64,405–412 (1991). This model is widely used to evaluate the antithrombotic potential of a variety of agents including heparin and the direct acting thrombin inhibitors.

Sprague Dawley rats weighing 375–450 g are anesthetized with sodium pentobarbital (50 mg/kg i.p.). Upon reaching an acceptable level of anesthesia, the ventral sur face of the neck is shaved and prepared for aseptic surgery. Electrocardiogram electrodes are connected and lead II is monitored throughout the experiment. The right femoral vein and artery are cannulated with PE-50 tubing for administration of a compound according to the invention and for obtaining blood samples and monitoring blood pressure, respectively. A midline incision is made in the ventral surface of the neck. The trachea is exposed and intubated with PE-240 tubing to ensure airway patency. The right carotid artery is isolated and two 4-0 silk sutures are placed around the vessel to facilitate instrumentation. An electromagnetic flow probe (0.95–1.0 mm lumen) is placed around the vessel to measure blood flow. Distal to the probe a 4×4 mm strip of parafilm is placed under the vessel to isolate it from the surrounding muscle bed. After baseline flow measurements are made, a 2×5 mm strip of filter paper previously saturated in 35% $FeCl_2$ is placed on top of the vessel downstream from the probe for ten minutes and then removed. The $FeCl_2$ is thought to diffuse into the underlying segment of artery and cause deendothelialization resulting in acute thrombus formation. Following application of the $FeCl_2$-soaked filter paper, blood pressure, carotid artery blood flow and heart rate are monitored for an im observation period of 60 minutes. Following occlusion of the vessel (defined as the attainment of zero blood flow), or 60 minutes after filter paper application if patency is maintained, the artery is ligated proximal and distal to the area of injury and the vessel is excised. The thrombus is removed and weighed immediately and recorded as the primary end point of the study.

Following surgical instrumentation a control blood sample (B1) is drawn. All blood samples are collected from the arterial catheter and mixed with sodium citrate to prevent clotting. After each blood sample, the catheter is flushed with 0.5 mL of 0.9% saline. A compound according to the invention is administered intravenously (i.v.) starting 5 minutes prior to $FeCl_2$ application. The time between $FeCl_2$ application and the time at which carotid blood flow reached zero is recorded as time to occlusion (TTO). For vessels that did not occlude within 60 minutes, TTO is assigned a value of 60 minutes. Five minutes after application of $FeCl_2$, a second blood sample is drawn (B2). After 10 minutes of $FeCl_2$ exposure, the filter paper is removed from the vessel and the animal is monitored for the remainder of the experiment. Upon reaching zero blood flow blood a third blood sample is drawn (B3) and the clot is removed and weighed. Template bleeding time measurements are performed on the forelimb toe pads at the same time that blood samples are obtained. Coagulation profiles consisting of activated partial thromboplastin time (APTT) and prothrombin time (PT) are performed on all blood samples. In some instances a compound according to the invention may be administered orally. Rats are restrained manually using standard techniques and compounds are administered by intragastric gavage using a 18 gauge curved dosing needle (volume of 5 mL/kg). Fifteen minutes after intragastric dosing, the animal is anesthetized and instrumented as described previously. Experiments are then performed according to the protocol described above.

The present invention may be embodied in other specific forms without departing from the spirit or essential attributes thereof.

What is claimed is:

1. A compound of the formula

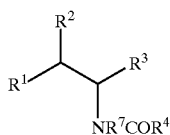
(I)

wherein

R¹ is a group of formula

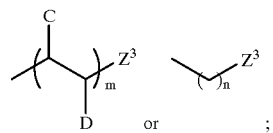

R² is hydrogen, —CO₂R⁵, —C(O)R⁵, —CONR⁵R⁵, —CH₂OR⁶ or —CH₂SR⁶;

R³ is hydrogen, optionally substituted alkyl, Z¹-alkyl, or a group of formula

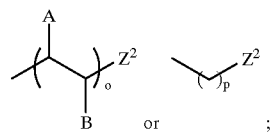

R⁴ is alkyl, alkenyl, alkynyl, optionally substituted cycloalkyl, optionally substituted cycloalkenyl, optionally substituted heterocyclyl, optionally substituted heterocyclenyl, optionally substituted aryl, optionally substituted heteroaryl, optionally substituted aralkyl, optionally substituted heteroaralkyl, optionally substituted aralkenyl, optionally substituted heteroaralkenyl, optionally substituted aralkynyl, or optionally substituted heteroaralkynyl;

R⁵ is hydrogen or lower alkyl;

R⁶ is hydrogen, lower alkyl, Z²-(lower alkyl), lower acyl, aroyl or heteroaroyl;

R⁷ is hydrogen or lower alkyl;

A and B are hydrogen or taken together are a bond;

C and D are hydrogen or taken together are a bond;

Z¹ is R⁶O— or R⁶S— or Y¹Y²N—;

Z² is optionally substituted aryl, optionally substituted heteroaryl, optionally substituted cycloalkyl, optionally substituted cycloalkenyl, optionally substituted heterocyclyl, and optionally substituted heterocyclenyl;

Z³ is piperidine optionally substituted with amidine or tetrahydropiperidine optionally substituted with amidine;

Y¹ and Y² are independently hydrogen, alkyl, aryl, aralkyl, acyl or aroyl; and m and o are independently 1 or 2;

n and p are independently 0, 1 or 3; or a pharmaceutically acceptable salt thereof, an N-oxide thereof, a solvate thereof, an acid bioisostere thereof, or prodrug thereof, wherein said amidine of Z³ has the structure —C(=NR¹¹)—NHR¹⁰ wherein R¹¹ is selected from the group consisting of hydrogen, R¹²O₂C—, R¹²O—, HO—, R¹²C(O)—, HCO—, cyano, optionally substituted lower alkyl, nitro or Y¹ᵃY²ᵃN—; and R¹⁰ is selected from the group consisting of hydrogen, HO—, optionally substituted lower alkyl, optionally substituted aralkyl, optionally substituted heteroaralkyl, and R¹²O₂C—; and wherein R¹² is alkyl, optionally substituted aralkyl, or optionally substituted heteroaralkyl and Y¹ᵃ and Y²ᵃ are independently hydrogen or alkyl.

2. The compound according to claim 1, wherein Z³ is said amidine, and R¹⁰ and R¹¹ are independently optionally substituted lower alkyl.

3. The compound according to claim 1 wherein Z³ is substituted by said amidine, and R¹⁰ and R¹¹ are independently hydrogen, HO—, or R¹²O₂C—.

4. The compound according to claim 1 wherein R² is hydrogen, —CO₂R⁵, —CH₂OR⁶ or —CH₂SR⁶.

5. The compound according to claim 1 wherein R² is hydrogen, —CO₂R⁵ or —CH₂OR⁶.

6. The compound according to claim 1 wherein R² is —CO₂R⁵ and R⁵ is lower alkyl.

7. The compound according to claim 1 wherein R² is —CH₂OR⁶ or —CH₂SR⁶ and R⁶ is hydrogen or lower alkyl.

8. The compound according to claim 1 wherein R³ is lower alkyl, R⁶O(lower alkyl)-, or a group of formula

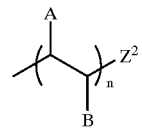

where A and B are hydrogen and n is 1.

9. The compound according to claim 1 wherein R⁴ is optionally substituted cycloalkyl, optionally substituted heterocyclyl, optionally substituted aryl, optionally substituted heteroaryl, optionally substituted aralkyl or optionally substituted aralkynyl.

10. The compound according to claim 1 wherein R⁴ is optionally substituted phenyl, optionally substituted naphthyl, or optionally substituted heteroaryl.

11. The compound according to claim 1 wherein R⁴ is optionally substituted (phenyl substituted phenyl), optionally substituted (heteroaryl substituted phenyl), optionally substituted (phenyl substituted heteroaryl) or optionally substituted (heteroaryl substituted heteroaryl).

12. The compound according to claim 1 wherein R⁵ is lower alkyl.

13. The compound according to claim 1 wherein R⁶ is hydrogen or lower alkyl.

14. The compound according to claim 1 wherein R⁷ is hydrogen.

15. The compound according to claim 1 wherein R⁸ and R⁹ are hydrogen.

16. The compound according to claim 1 wherein R¹² is lower alkyl.

17. The compound according to claim 1 wherein n is 1.

18. The compound according to claim 1 wherein Z³ is substituted by, at least, an amidino group in the meta or para position of the ring system of Z³, relative to the position of attachment of Z³ to the rest of the molecule.

19. The compound according to claim 1 wherein Z¹ is optionally substituted aryl.

20. The compound according to claim 1 wherein Z¹ is phenyl.

21. The compound according to claim 1 wherein R¹ is a group of formula

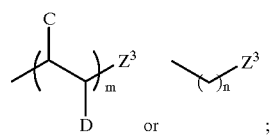

m and n are 1; C and D are hydrogen; and

Z³ is piperidine optionally substituted with amidine or tetrahydropiperidine optionally substituted with amidine.

22. The compound according to claim 1 wherein

Z³ is substituted by said amidine;

$R^{10}$ and $R^{11}$ are hydrogen;

$R^2$ is hydrogen, —CO$_2$R$^5$, —C(O)R$^5$, —CH$_2$OR$^6$ or —CH$_2$SR$^6$;

$R^3$ is hydrogen, alkyl or Z¹-alkyl, or a group of formula

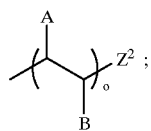

$R^4$ is optionally substituted cycloalkyl, optionally substituted cycloalkenyl, optionally substituted heteroaryl, optionally substituted fused arylcycloalkyl, optionally substituted fused arylcycloalkyl, optionally substituted fused arylcycloalkenyl, optionally substituted fused arylheteroaryl, optionally substituted fused heteroarylaryl, optionally substituted fused heteroarylcycloalkyl, optionally substituted fused heteroarylcycloalkenyl, optionally substituted fused heteroarylheterocyclyl, optionally substituted fused heteroarylheterocyclenyl;

$R^6$ is hydrogen or lower alkyl;

A, B, C and D, $R^7$ are hydrogen;

Q is R⁶O—; o and m are 1; n is 1 or 3; or a pharmaceutically acceptable salt thereof, an N-oxide thereof or prodrug thereof.

23. A compound according to claim 1 which is:

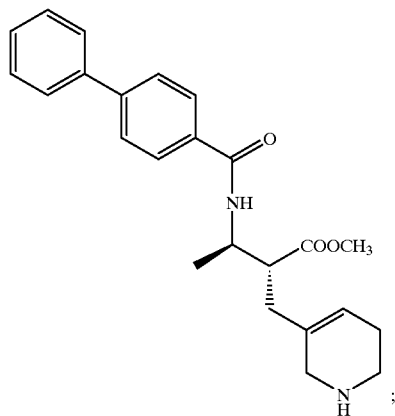

-continued

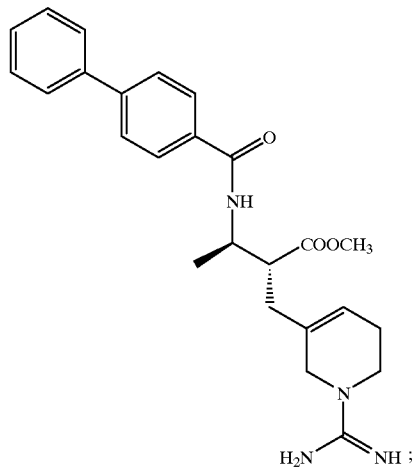

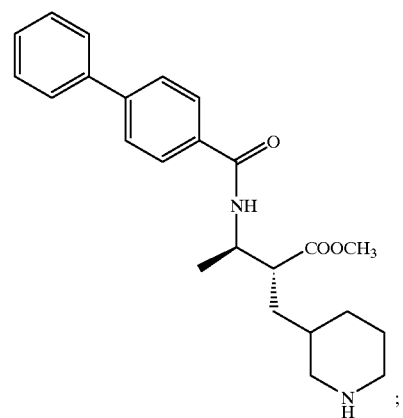

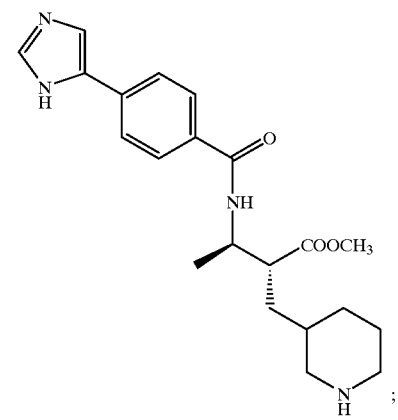

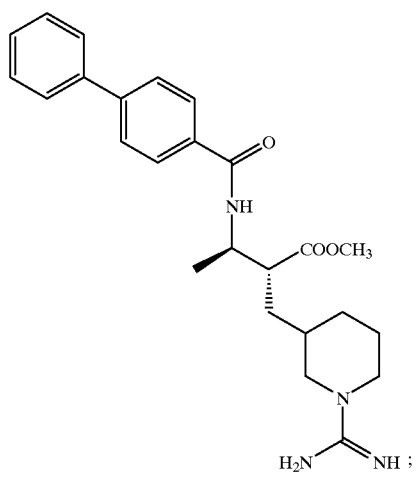
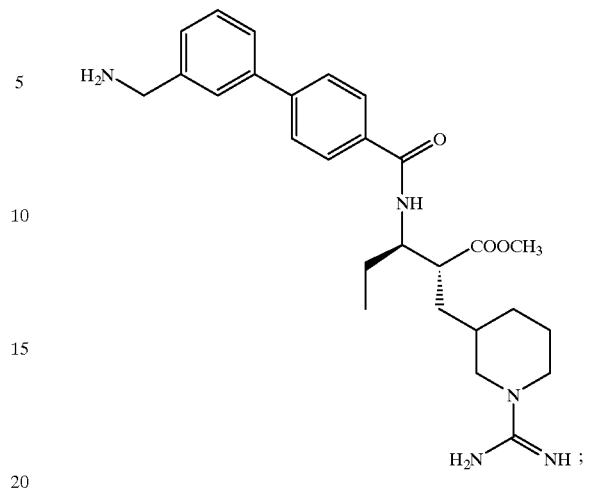
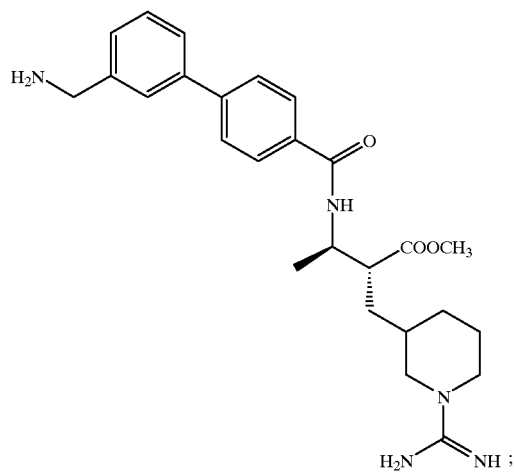
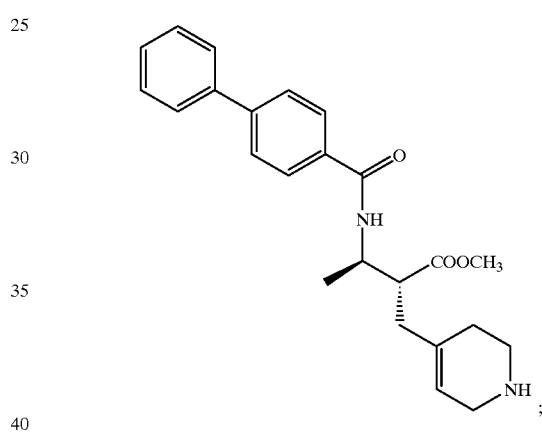
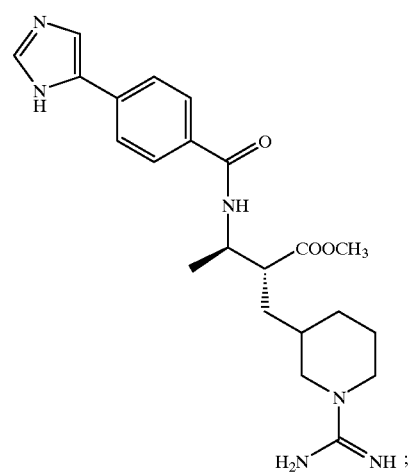
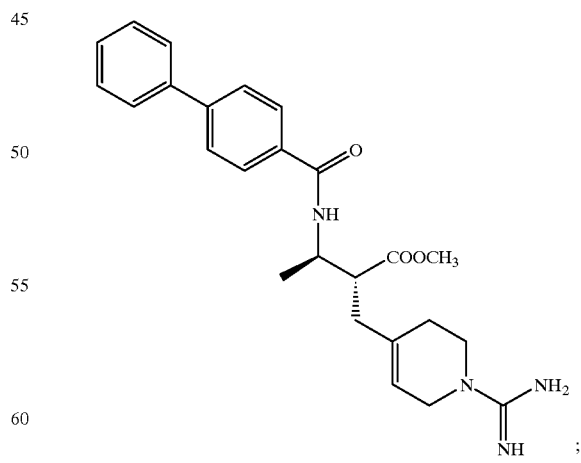

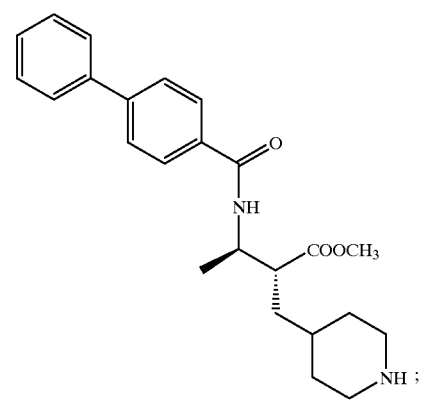
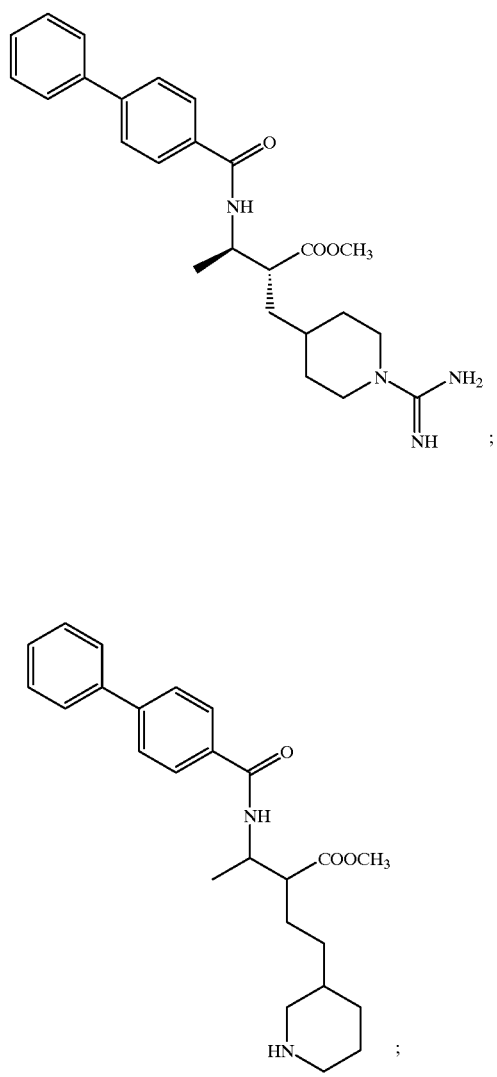

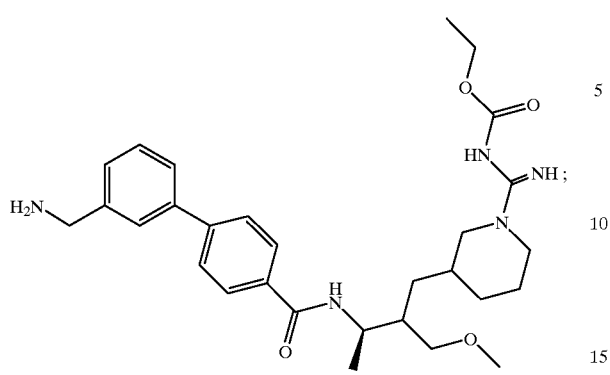
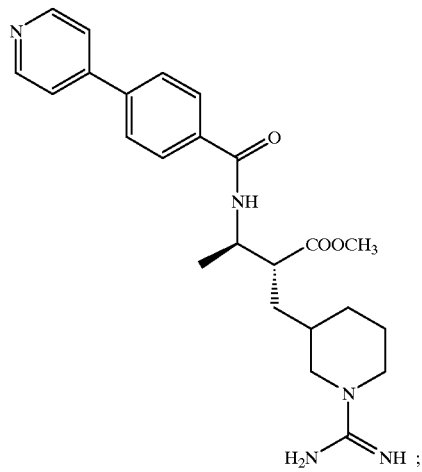
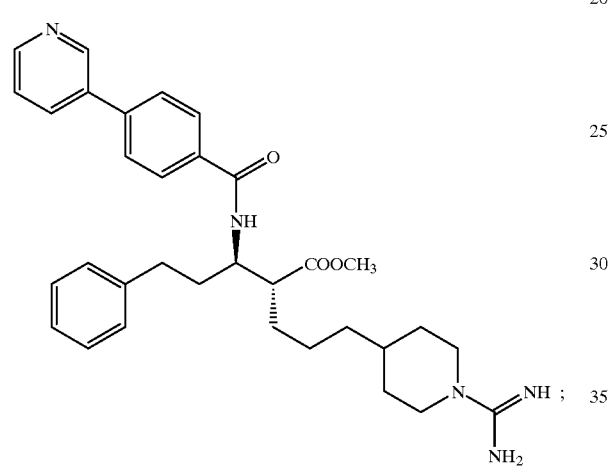
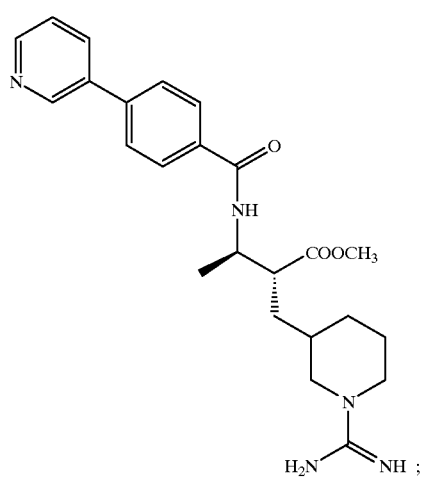
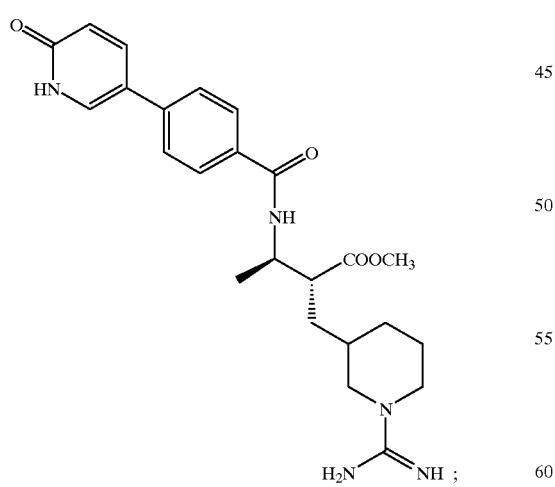
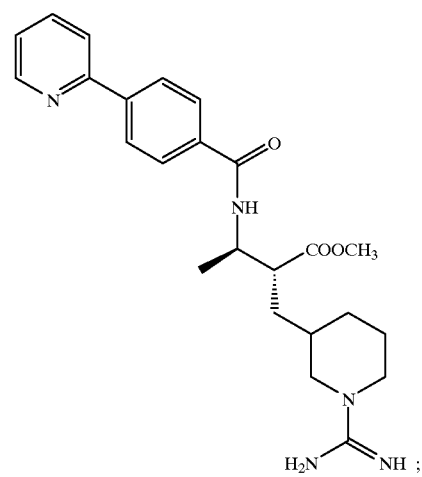

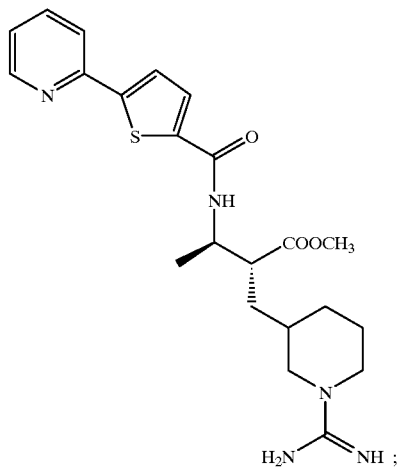
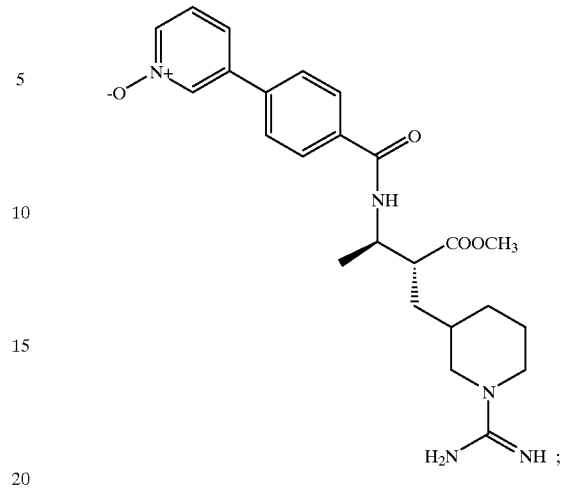
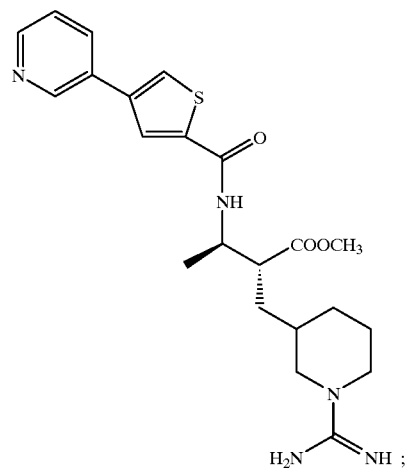
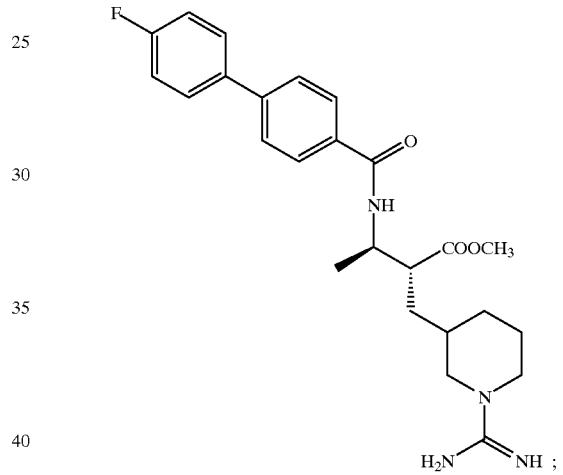
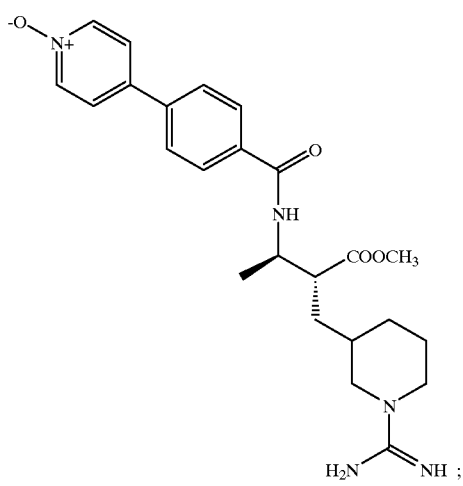
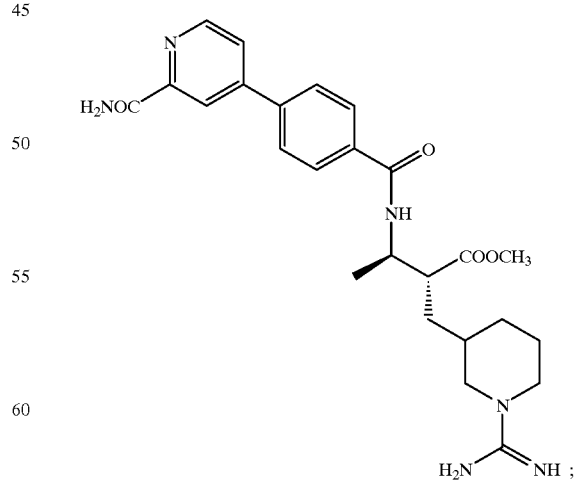

-continued
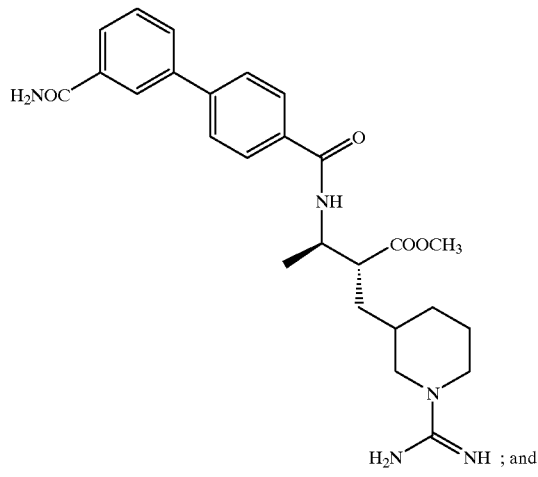
; and
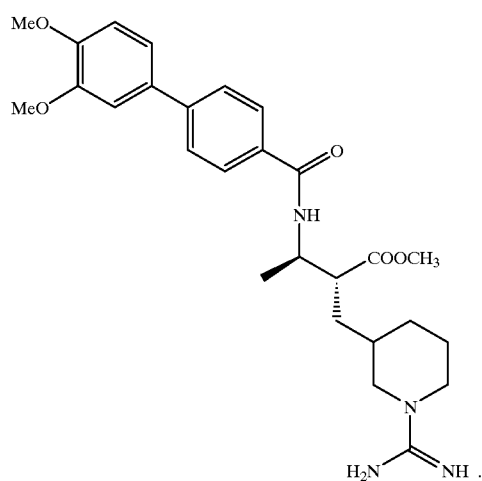
.
24. A compound according to claim 1 which is:
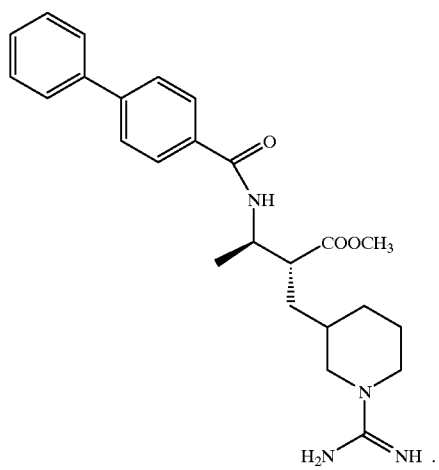
.
25. A compound according to claim 1 which is:
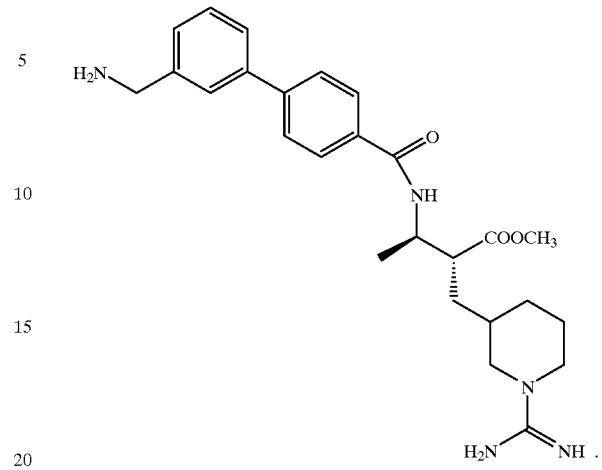
.
26. A compound according to claim 1 which is:
27. A compound according to claim 1 which is:
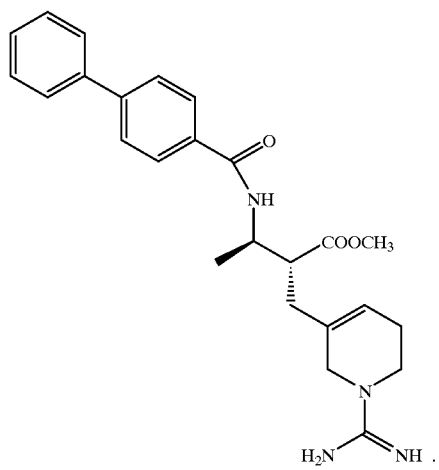
.

28. A compound according to claim 1 which is:

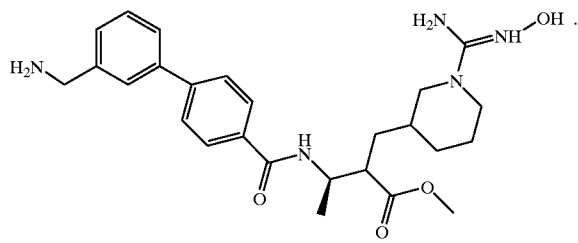

29. A pharmaceutical composition comprising a therapeutically effective amount of the compound according to claim 1 and a pharmaceutically acceptable carrier.

30. A method for inhibiting coagulation in whole blood or biological samples comprising administering an anticoagulating effective amount of the compound of claim 1.

31. A method for inhibiting Factor Xa activity in a patient in need thereof comprising administering to said patient a therapeutically effective amount of the compound according to claim 1.

32. A method for inhibiting thrombin formation in a patient in need thereof, comprising administering to said patient a therapeutically effective amount of the compound according to claim 1.

33. A compound of the formula

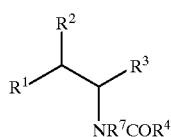

(I)

wherein $R^1$ is a group of formula

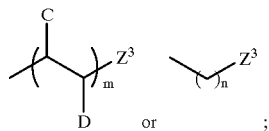

$R^2$ is hydrogen, $-CO_2R^5$, $-C(O)R^5$, $-CONR^5R^5$, $-CH_2OR^6$ or $-CH_2SR^6$;

$R^3$ is hydrogen, optionally substituted alkyl, $Z^1$-alkyl, or a group of formula

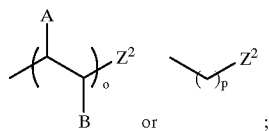

$R^4$ is alkyl, alkenyl, alkynyl, optionally substituted cycloalkyl, optionally substituted cycloalkenyl, optionally substituted heterocyclyl, optionally substituted heterocyclenyl, optionally substituted aryl, optionally substituted heteroaryl, optionally substituted aralkyl, optionally substituted heteroaralkyl, optionally substituted aralkenyl, optionally substituted heteroaralkenyl, optionally substituted aralkynyl, or optionally substituted heteroaralkynyl;

$R^5$ is hydrogen or lower alkyl;

$R^6$ is hydrogen, lower alkyl, $Z^2$-(lower alkyl), lower acyl, aroyl or heteroaroyl;

$R^7$ is hydrogen or lower alkyl;

A and B are hydrogen or taken together are a bond;

C and D are hydrogen or taken together are a bond;

$Z^1$ is $R^6O-$ or $R^6S-$ or $Y^1Y^2N-$;

$Z^2$ is optionally substituted aryl, optionally substituted heteroaryl, optionally substituted cycloalkyl, optionally substituted cycloalkenyl, optionally substituted heterocyclyl, and optionally substituted heterocyclenyl;

$Z^3$ is piperidine optionally substituted with amidine or tetrahydropiperidine optionally substituted with amidine;

$Y^1$ and $Y^2$ are independently hydrogen, alkyl, aryl, aralkyl, acyl or aroyl;

m and o are independently 1 or 2; and n and p are independently 0, 1 or 3; or a pharmaceutically acceptable salt thereof, an N-oxide thereof, a solvate thereof, an acid bioisostere thereof, or prodrug thereof.

34. The compound according to claim 33 wherein $R^4$ is optionally substituted phenyl, optionally substituted naphthyl, or optionally substituted heteroaryl.

35. The compound according to claim 34 wherein $R^4$ is optionally substituted (phenyl substituted phenyl), optionally substituted (heteroaryl substituted phenyl), optionally substituted (phenyl substituted heteroaryl) or optionally substituted (heteroaryl substituted heteroaryl).

36. A pharmaceutical composition comprising a therapeutically effective amount of the compound according to claim 33 and a pharmaceutically acceptable carrier.

37. A method for inhibiting coagulation in whole blood or biological samples comprising administering an anticoagulating effective amount of a compound of claim 33.

38. A method for inhibiting Factor Xa activity in a patient in need thereof comprising administering to said patient a therapeutically effective amount of a compound according to claim 33.

39. A method for inhibiting thrombin formation in a patient in need thereof, comprising administering to said patient a therapeutically effective amount of a compound according to claim 33.

* * * * *